(12) United States Patent
Miller

(10) Patent No.: US 10,126,296 B2
(45) Date of Patent: *Nov. 13, 2018

(54) IMMUNOASSAY METHOD AND DEVICE WITH MAGNETICALLY SUSCEPTIBLE BEAD CAPTURE

(75) Inventor: Cary James Miller, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 348 days.

This patent is subject to a terminal disclaimer.

(21) Appl. No.: 13/204,109

(22) Filed: Aug. 5, 2011

(65) Prior Publication Data
US 2012/0031773 A1 Feb. 9, 2012

Related U.S. Application Data

(60) Provisional application No. 61/371,066, filed on Aug. 5, 2010.

(51) Int. Cl.
*G01N 33/00* (2006.01)
*G01N 33/543* (2006.01)
*B01L 3/00* (2006.01)

(52) U.S. Cl.
CPC .. *G01N 33/54326* (2013.01); *B01L 3/502761* (2013.01); *G01N 33/5438* (2013.01); *B01L 2200/0668* (2013.01); *B01L 2400/043* (2013.01); *B01L 2400/0487* (2013.01)

(58) Field of Classification Search
None
See application file for complete search history.

(56) References Cited

U.S. PATENT DOCUMENTS

| | | |
|---|---|---|
| 4,230,685 A | 10/1980 | Senyei et al. |
| 4,554,088 A | 11/1985 | Whitehead et al. |
| 4,628,037 A | 12/1986 | Chagnon et al. |
| 4,849,340 A | 7/1989 | Oberhardt |
| 4,945,045 A | 7/1990 | Forrest et al. |
| 4,978,610 A | 12/1990 | Forrest et al. |
| 5,149,630 A | 9/1992 | Forrest et al. |
| 5,200,051 A | 4/1993 | Cozzette et al. |
| 5,422,621 A | 6/1995 | Gambino et al. |
| 5,445,971 A | 8/1995 | Rohr |
| 5,554,339 A | 9/1996 | Cozzette et al. |
| 5,587,102 A | 12/1996 | Stern et al. |
| 5,821,399 A | 10/1998 | Zelin |

(Continued)

FOREIGN PATENT DOCUMENTS

| | | |
|---|---|---|
| WO | WO 00/51814 | 9/2000 |
| WO | WO 01/87458 | 11/2001 |

OTHER PUBLICATIONS

K&J Magnetics (kjmagnetics.com, neodymium cylinder magnets, D22-N52). http://www.kjmagnetics.com/proddetail.asp?prod=D22-N52.*

(Continued)

*Primary Examiner* — Melanie Yu Brown
*Assistant Examiner* — Richard Moerschell
(74) *Attorney, Agent, or Firm* — Kilpatrick Townsend & Stockton LLP

(57) ABSTRACT

The present invention provides apparatus and methods for the rapid determination of analytes in liquid samples by immunoassays incorporating magnetic capture of beads on a sensor capable of being used in the point-of-care diagnostic field.

34 Claims, 36 Drawing Sheets

(56) References Cited

U.S. PATENT DOCUMENTS

| | | | |
|---|---|---|---|
| 5,843,329 | A | 12/1998 | Deetz |
| 5,998,224 | A | 12/1999 | Rohr et al. |
| 6,231,760 | B1 | 5/2001 | Siddiqi |
| 6,294,342 | B1 | 9/2001 | Rohr et al. |
| 6,325,973 | B1 | 12/2001 | Leland et al. |
| 6,548,311 | B1 | 4/2003 | Knoll |
| 6,764,859 | B1 | 7/2004 | Kreuwel et al. |
| 7,106,051 | B2 | 9/2006 | Prins et al. |
| 7,223,438 | B2 | 5/2007 | Mirkin et al. |
| 7,419,821 | B2 * | 9/2008 | Davis ............. B01L 3/502723 422/50 |
| 7,572,355 | B1 | 8/2009 | Arumugam |
| 7,682,833 | B2 | 3/2010 | Miller et al. |
| 7,723,099 | B2 * | 5/2010 | Miller et al. ............. 435/287.1 |
| 8,084,272 | B2 | 12/2011 | Campbell et al. |
| 9,233,370 | B2 * | 1/2016 | Miller ............. B01L 3/502761 |
| 2002/0039667 | A1 | 4/2002 | Takaya et al. |
| 2003/0012693 | A1 * | 1/2003 | Otillar ............. B01J 19/0046 506/39 |
| 2003/0040129 | A1 | 2/2003 | Shah |
| 2003/0170881 | A1 * | 9/2003 | Davis ............. B01L 3/502723 435/287.2 |
| 2004/0009614 | A1 | 1/2004 | Ahn et al. |
| 2004/0210289 | A1 | 10/2004 | Wang et al. |
| 2005/0054078 | A1 | 3/2005 | Miller et al. |
| 2006/0134713 | A1 * | 6/2006 | Rylatt ............. G01N 33/54326 435/7.92 |
| 2006/0207877 | A1 | 9/2006 | Schmidt et al. |
| 2006/0257854 | A1 | 11/2006 | McDevitt et al. |
| 2006/0292700 | A1 | 12/2006 | Wang et al. |
| 2008/0035579 | A1 | 2/2008 | Lee et al. |
| 2008/0160634 | A1 * | 7/2008 | Su ............. G01N 27/745 436/501 |
| 2008/0187472 | A1 | 8/2008 | Ahn et al. |
| 2008/0240983 | A1 * | 10/2008 | Harris ............. G01N 35/00584 422/52 |
| 2009/0001983 | A1 | 1/2009 | Wittkowski |
| 2009/0068757 | A1 | 3/2009 | Lehmann et al. |
| 2009/0148847 | A1 * | 6/2009 | Kokoris ............. B01F 11/0071 435/6.14 |
| 2009/0191401 | A1 | 7/2009 | Deetz |
| 2010/0009456 | A1 * | 1/2010 | Prins ............. G01N 33/558 436/164 |
| 2010/0015728 | A1 * | 1/2010 | Dilleen ............. G01N 33/54326 436/536 |
| 2010/0140146 | A1 | 6/2010 | Markov et al. |
| 2010/0248273 | A1 | 9/2010 | Campbell et al. |
| 2011/0053289 | A1 | 3/2011 | Lowe et al. |
| 2011/0071044 | A1 | 3/2011 | Horiuchi |
| 2011/0117580 | A1 | 5/2011 | Campbell et al. |
| 2011/0117581 | A1 | 5/2011 | Campbell et al. |
| 2011/0150705 | A1 | 6/2011 | Doyle et al. |
| 2011/0306070 | A1 | 12/2011 | Campbell et al. |
| 2012/0034624 | A1 * | 2/2012 | Miller ............. G01N 33/54333 435/7.4 |
| 2012/0034633 | A1 * | 2/2012 | Miller et al. ............. 435/7.94 |
| 2012/0034684 | A1 * | 2/2012 | Campbell ............. G01N 33/54333 435/287.2 |
| 2012/0295302 | A1 | 11/2012 | Lamish et al. |
| 2013/0217144 | A1 | 8/2013 | Rida |
| 2016/0109439 | A1 | 4/2016 | Miller et al. |
| 2016/0216256 | A1 | 7/2016 | Miller et al. |

OTHER PUBLICATIONS

Kuhn "Developing Multiplexed Assays for Troponin I and Interleukin-33 in Plasma by Peptide Immunoaffinity Enrichment and Targeted Mass Spectrometry" Clinical Chemistry 55:6 1108-1117, Supplemental methods pp. 1-8. 2009.*

Berti el al, "Microfluidic-based electrochemical genosensor coupled to magnetic beads for hybridization detection", TALANTA, vol. 77, No. 3, Jan. 15, 2009 (Jan. 15, 2009), pp. 971-978.*

Ramanujan, "Magnetic particles for biomedical applications", Chapter 17, Biomedical Materials, Springer, NY, 2009.*

K&J Magnetics (kjmagnetics.com, neodymium cylinder magnets, D22-N52).*

Rossier "Plasma etched polymer microelectrochemical systems" Lab Chip 2002, 2, 145-150.*

Rossier, et al., "Plasma Etched Polymer Microelectrochemical Systems," Lab Chip, 2002, 2, pp. 145-150.

Rossier, et al., Journal of Laboratory Automation, Dec. 2008, vol. 13, No. 6, pp. 322-329.

Ramanujan, "Magnetic Particles for Biomedical Applicatoins," Chapter 17, Biomedical Materials, Springer, NY, 2009.

Kuhn, et al., "Developing Multiplexed Assays for Troponin I and Interleukin-33 in Plasma by Peptide Immunoaffinity Enrichment and Targeted Mass Spectrometry," Clinical Chemistry, vol. 55, No. 6, pp. 1108-1117.

Office Action for U.S. Appl. No. 13/204,121 dated Nov. 9, 2012.

Berti et al., "Microfluidic-based electrochemical genosensor coupled to magnetic beads for hybridization detection", vol. 77, No. 3, Jan. 15, 2009, pp. 971-978.

International Search Report and Written Opinion for PCT/US2011/046757 dated Oct. 12, 2011.

International Search Report and Written Opinion for PCT/US2011/046758 dated Oct. 7, 2011.

International Search Report and Written Opinion for PCT/US2011/046761 dated Oct. 7, 2011.

Estes et al., "On chip cell separator using magnetic bead-based enrichment depletion of various surface markers", Biomed Microdevices (2009), 11: 509-515.

Laurrell et al., Methods in Enzymology, vol. 73, "Electroimmunoassay", Academic Press, New York, 339, 340, 346-348 (1981).

M.J. Green (1987) Philos. Trans. R. Soc. Lond. B. Biol. Sci. 316: 135-142.

Bruls et al., Lab Chip 9, 3504-3510 (2009) (Abstract only).

Dittmer et al., Clin. Chim. Acta (2010), doi: 10.1016/j.cca.2010.03.001 (Abstract only).

Peng, Z-C, et al., "A Bead-Based Electrochemical Biosensor with Integrated magnetic Manipulation for Controllable Sample Preconcentration," Solid-State Sensors, Actuators and Microsystems Conference, 2009. Transducers (2009): 1802-1805.

International Search Report and Written Opinion for PCT/US2011/046753 dated Dec. 30, 2011.

International Preliminary Report on Patentability dated Feb. 14, 2013 in corresponding International Application No. PCT/US2011/046753.

Office Action for corresponding European Appl. No. 11746727.4-1408 dated Jun. 4, 2014.

Kim, et al., "Fabrication of comb interdigitated electrodes array (IDA) for a microbead-based electrochemical assay system", Biosensors and Bioelectronics 20 (2004), pp. 887-894.

Office Action for U.S. Appl. No. 13/204,172 dated Jun. 5, 2014.

Office Action for corresponding Chinese Appl. No. 201180046212.8 dated Jun. 26, 2014.

Office Action for corresponding U.S. Appl. No. 13/204,121 dated Oct. 22, 2014.

Final Office Action dated Oct. 15, 2015 for U.S. Appl. No. 13/204,094, 57 pages.

Notice of Allowance dated Sep. 29, 2015 for U.S. Appl. No. 13/204,121, 8 pages.

United States Patent and Trademark Office, Office Action, U.S. Appl. No. 13/204,121 dated May 20, 2015.

Notice of Allowance issued in U.S. Appl. No. 13/204,172, dated Feb. 26, 2016.

"Final Office Action", dated Jul. 24, 2013, issued in U.S. Appl. No. 13/204,094, 27 pages.

"Non-Final Office Action", dated Mar. 28, 2013, issued in U.S. Appl. No. 13/204,094, 29 pages.

"Non-Final Office Action", dated Jan. 29, 2015, issued in U.S. Appl. No. 13/204,094, 53 pages.

"Final Office Action", dated Nov. 1, 2013, issued in U.S. Appl. No. 13/204,121, 14 pages.

"Non-Final Office Action", dated Apr. 24, 2013, issued in U.S. Appl. No. 13/204,121, 12 pages.

(56) References Cited

OTHER PUBLICATIONS

"Final Office Action", dated Feb. 10, 2015, issued in U.S. Appl. No. 13/204,172, 18 pages.
"Non-Final Office Action" issued in U.S. Appl. No. 13/204,094, dated Jul. 25, 2017, 46 pages.
"Notice of Allowance" issued in U.S. Appl. No. 14/976,318, dated Jan. 18, 2018, 12 pages.
"Notice of Allowance" issued in U.S. Appl. No. 14/976,318, dated Mar. 8, 2018, 13 pages.
"Non-Final Office Action" issued in U.S. Appl. No. 15/086,340, dated Dec. 27, 2017, 8 pages.
"Final Office Action" issued in U.S. Appl. No. 13/204,094, dated Apr. 3, 2018, 46 pages.
"Notice of Allowance" issued in U.S. Appl. No. 15/086,340, dated May 7, 2018, 9 pages.
"Non-Final Office Action" issued in U.S. Appl. No. 13/204,094, dated Sep. 7, 2018, 52 pages.
"Notice of Allowance" issued in U.S. Appl. No. 15/938,141, dated Aug. 8, 2018, 10 pages.
Rossier et al., "Chapter 36 Microfluidic-based Electrochemical Platform for Rapid Immunological Analysis in Small Volumes", Comprehensive Analytical Chemistry 49 Alegret and Merkoc, vol. 49, 2007, pp. 885-905.

\* cited by examiner

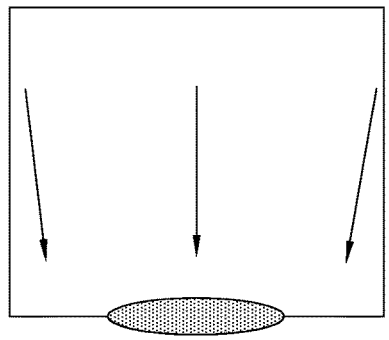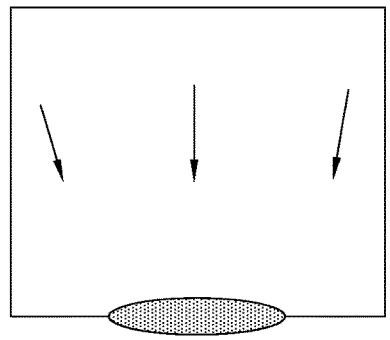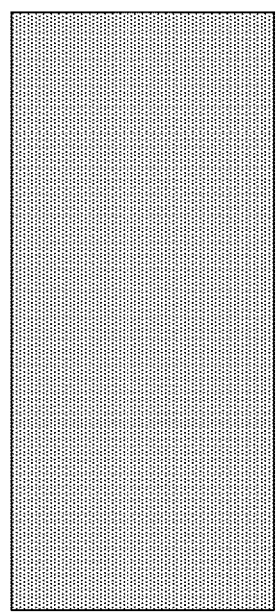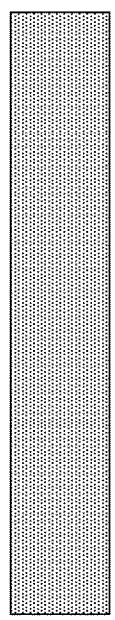
d=1mm                d=0.3mm
FIG. 4

Magnetic Bead Capture Site:
Screen Printed Line Magnet

Magnetic Bead Capture Site:
Bulk Magnet

IMMUNOASSAY METHOD AND DEVICE WITH MAGNETICALLY SUSCEPTIBLE BEAD CAPTURE

CROSS REFERENCE TO RELATED APPLICATION

The present invention claims priority to U.S. Provisional Application No. 61/371,066, filed on Aug. 5, 2010, the entire contents and disclosures of which are hereby incorporated by reference.

FIELD OF THE INVENTION

The present invention generally relates to an apparatus and method for rapid determination of analytes in liquid samples by immunoassays incorporating magnetic capture of beads on a sensor, capable of being used in the point-of-care diagnostic field, including, for example, use at accident sites, emergency rooms, in surgery, in intensive care units, and also in non-medical environments.

BACKGROUND OF THE INVENTION

A multitude of laboratory immunoassay tests for analytes of interest are performed on biological samples for diagnosis, screening, disease staging, forensic analysis, pregnancy testing and drug testing, among others. While a few qualitative tests, such as pregnancy tests, have been reduced to simple kits for a patient's home use, the majority of quantitative tests still require the expertise of trained technicians in a laboratory setting using sophisticated instruments. Laboratory testing increases the cost of analysis and delays the patient's receipt of the results. In many circumstances, this delay can be detrimental to the patient's condition or prognosis, such as for example the analysis of markers indicating myocardial infarction and heart failure. In these and similar critical situations, it is advantageous to perform such analyses at the point-of-care, accurately, inexpensively and with minimal delay.

Many types of immunoassay devices and processes have been described. For example, a disposable sensing device for measuring analytes by means of immunoassay in blood is disclosed by Davis et al. in U.S. Pat. No. 7,419,821. This device employs a reading apparatus and a cartridge that fits into the reading apparatus for the purpose of measuring analyte concentrations. A potential problem with such disposable devices is variability of fluid test parameters from cartridge to cartridge due to manufacturing tolerances or machine wear. U.S. Pat. No. 5,821,399 to Zelin discloses methods to overcome this problem using automatic flow compensation controlled by a reading apparatus having conductimetric sensors located within a cartridge. Each of these patents is hereby incorporated by reference in their respective entireties.

Electrochemical detection, in which the binding of an analyte directly or indirectly causes a change in the activity of an electroactive species adjacent to an electrode, has also been applied to immunoassays. For an early review of electrochemical immunoassays, see Laurell et al., Methods in Enzymology, vol. 73, "Electroimmunoassay", Academic Press, New York, 339, 340, 346-348 (1981).

In an electrochemical immunosensor, the binding of an analyte to its cognate antibody produces a change in the activity of an electroactive species at an electrode that is poised at a suitable electrochemical potential to cause oxidation or reduction of the electroactive species. There are many arrangements for meeting these conditions. For example, electroactive species may be attached directly to an analyte, or the antibody may be covalently attached to an enzyme that either produces an electroactive species from an electroinactive substrate or destroys an electroactive substrate. See, M. J. Green (1987) Philos. Trans. R. Soc. Lond. B. Biol. Sci. 316:135-142, for a review of electrochemical immunosensors. Magnetic components have been integrated with electrochemical immunoassays. See, for example, U.S. Pat. Nos. 4,945,045; 4,978,610; and 5,149,630, each to Forrest et al. Furthermore, jointly-owned U.S. Pat. No. 7,419,821 to Davis et al. (referenced above) and U.S. Pat. Nos. 7,682,833 and 7,723,099 to Miller et al. teach immunosensing with magnetic particles.

Microfabrication techniques (e.g., photolithography and plasma deposition) are attractive for construction of multilayered sensor structures in confined spaces. Methods for microfabrication of electrochemical immunosensors, for example on silicon substrates, are disclosed in U.S. Pat. No. 5,200,051 to Cozette et al., which is hereby incorporated in its entirety by reference. These include dispensing methods, methods for attaching biological reagent, e.g., antibodies, to surfaces including photoformed layers and microparticle latexes, and methods for performing electrochemical assays.

U.S. Pat. No. 7,223,438 to Mirkin et al. describes a method of forming magnetic nanostructures by depositing a precursor onto a substrate using a nanoscopic tip, and then converting the precursor to form a magnetic nanostructure. U.S. Pat. No. 7,106,051 to Prins et al. describes a magnetoresistive sensing device for determining the density of magnetic particles in a fluid.

U.S. Pat. Appl. Pub. 2009/0191401 to Deetz et al. is directed to magnetic receptive paints and coatings that allow magnets to stick to coated surfaces. These paint and coating compositions contain multiple-sized ferromagnetic particles and a base resin with minimal or no fillers and provide an ultra smooth finish on a substrate. U.S. Pat. No. 5,587,102 to Stern et al. discloses a latex paint composition comprising iron particles and U.S. Pat. No. 5,843,329 to Deetz provides techniques for blending magnetic receptive particles into solution for making magnetic coatings. Jointly-owned U.S. Pat. Nos. 5,998,224 and 6,294,342 to Rohr et al. disclose assay methods utilizing the response of a magnetically responsive reagent to influence a magnetic field to qualitatively or quantitatively measure binding between specific binding pair members. Each of these patents is hereby incorporated by reference in its entirety.

Both an integrated biosensor for multiplexed immunoassays based on actuated magnetic nanoparticles and a high sensitivity point-of-care test for cardiac troponin based on an optomagnetic biosensor have been described. See, Bruls et al., Lab Chip 9, 3504-3510 (2009) and Dittmer et al., Clin. Chim. Acta (2010), doi:10.1016/j.cca.2010.03.001, respectively. There are numerous disclosures of the use of magnetically susceptible particles, e.g., U.S. Pat. No. 4,230,685 to Senyei et al., U.S. Pat. No. 4,554,088 to Whitehead et al., and U.S. Pat. No. 4,628,037 to Chagnon et al. An important factor in the use of these particles in assays is efficient mixing to enhance the reaction rate between the target analyte and the particle surfaces, as opposed to the use of a macro-binding surface that mainly relies on diffusion. Magnetic mixing systems are disclosed in U.S. Pat. No. 6,231,760 to Siddiqi and U.S. Pat. No. 6,764,859 to Kreuwel et al.

Notwithstanding the above literature, there remains a need in the art for improved immunosensing devices with greater sensitivity for the detection of analytes, including, for example, cardiac troponin I for early detection of myocardial infarction. These and other needs are met by the present invention as will become clear to one of skill in the art to which the invention pertains upon reading the following disclosure.

SUMMARY OF THE INVENTION

The present invention is directed to a magnetic immunosensing device and methods of performing an immunoassay with immunosensors incorporating magnetic capture of beads on a sensor to provide diverse real-time or near real-time analysis of analytes.

In one embodiment, the invention is directed to a magnetic immunosensing device for detecting an analyte in a sample, comprising: a sensing electrode on a substantially planar chip, wherein the electrode is positioned in a conduit for receiving a sample mixed with magnetically susceptible beads; and a high-field magnet, e.g., a permanent magnet or an electromagnet, positioned proximate to said chip for attracting the beads in the conduit substantially proximate to said electrode and substantially retaining the beads at said electrode surface during removal of the unbound sample and washing of said electrode, wherein the beads are coated with an antibody to an analyte in the sample.

Another embodiment of the present invention is directed to a method of performing a sandwich immunoassay for an analyte in a sample with a magnetic immunosensor, wherein said immunosensor comprises a sensing electrode on a substantially planar chip, wherein the electrode is positioned in a conduit for receiving a sample mixed with magnetically susceptible beads, and a high-field magnet, e.g., a permanent magnet or an electromagnet, positioned proximate to said chip, said method comprising: (a) mixing magnetically susceptible beads coated with a capture antibody with a sample containing an analyte and a signal antibody to form a sandwich on the beads; (b) applying the mixture to the immunosensor; (c) magnetically localizing and retaining at least a portion of the beads on the electrode; (d) washing the unbound sample from the electrode; (e) exposing the signal antibody of the sandwich to a signal generating reagent; and (f) measuring a signal from the reagent at the electrode.

In another embodiment, a method of performing a competitive immunoassay for an analyte in a sample with a magnetic immunosensor, wherein said immunosensor comprises a sensing electrode on a substantially planar chip, wherein the electrode is positioned in a conduit for receiving a sample mixed with magnetically susceptible beads, and a high-field magnet, e.g., a permanent magnet or an electromagnet, positioned below said chip, is provided. This method comprises: (a) mixing magnetically susceptible beads coated with a capture antibody with a sample containing an analyte and a labeled form of said analyte to permit competitive binding on the beads; (b) applying the mixture to the immunosensor; (c) magnetically localizing and retaining at least a portion of the beads on the electrode; (d) washing the unbound sample from the electrode; (e) exposing the localized analyte to a signal generating reagent; and (f) measuring a signal from the reagent at the electrode.

Certain embodiments of the invention are directed to a system comprising a reader and a single-use cartridge containing the immunosensor of the present invention. Various other embodiments of the invention are directed to a kit for performing an analyte immunoassay in a whole blood sample, comprising: magnetically susceptible beads; a sensing electrode on a substantially planar chip; and a high-field magnet, e.g., a permanent magnet or an electromagnet, positioned proximate to the chip for attracting the beads substantially proximate to the electrode and substantially retaining the beads at the electrode surface.

The above summary of the present invention is not intended to describe each illustrated embodiment or every implementation of the present invention. The figures and the detailed description that follow more particularly exemplify these embodiments.

BRIEF DESCRIPTION OF THE DRAWINGS

These and other objectives, features and advantages of the present invention are described in the following detailed description of the specific embodiments and are illustrated in the following Figures, in which:

FIG. 4 is a schematic of magnetic field lines for sensor configurations;

FIGS. 15A and 15B depict the over-printed magnetic layer in accordance with other embodiments of the present invention;

FIG. 22A shows a cross-section of the trench and FIG. 22B shows a different cross-section of the trench filled with NbFeB powder in a polyimide resin;

DETAILED DESCRIPTION OF THE INVENTION

Figure 1:
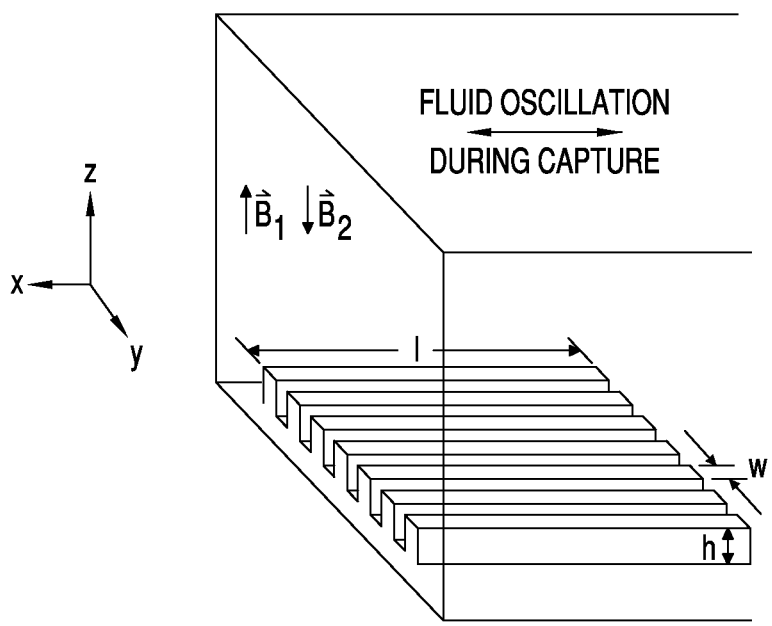
FIG. 1 is a cross-sectional illustration of a grooved immunosensor chip in a conduit with applied magnetic fields in accordance with one embodiment of the present invention.

The present invention relates to an apparatus and its method of use for determining the presence or concentrations of analytes in a liquid sample with a single-use disposable cartridge. The invention is adapted for conducting diverse real-time or near real-time assays of analytes. This invention is particularly relevant to high sensitivity cardiac troponin assays in whole blood samples.

In specific embodiments, the invention relates to the determination of analytes in biological samples such as blood using magnetic electrochemical immunosensors or other ligand/ligand receptor-based biosensors based on a magnetically susceptible bead localization step. The present invention also hereby incorporates by reference in their respective entireties jointly-owned U.S. Pat. No. 7,419,821 to Davis et al. and U.S. Pat. Nos. 7,682,833 and 7,723,099 to Miller et al., each of which is referenced above.

One notable advantage of the magnetically susceptible bead capture approach of the present invention is in improving the low-end sensitivity of immunoassays where there is a perceived benefit in detection of extremely low levels of a marker of myocardial injury (e.g., cTnI). Further advantages and benefits of the embodiments of the invention described and disclosed herein include but are not limited to ease of use, automation of many, if not all steps, of the analysis and elimination of user induced error in the analysis.

I. Magnetic Immunosensor

Various embodiments of the present invention are directed to a magnetic immunosensing device or immunosensor that includes a base sensor or sensing electrode on a substantially planar chip where the sensing electrode is positioned in a conduit for receiving a sample mixed with beads that can be attracted to a magnet, or respond to a magnetic field.

A high-field magnet, e.g., a permanent magnet or an electromagnet, is positioned proximate to the immunosensor chip (e.g., below) or incorporated into the immunosensor chip, for attracting the beads in the conduit substantially proximate to the sensing electrode. This magnetic zone functions to substantially retain the beads at or near the sensing electrode surface during removal of the unbound sample and washing of the electrode. As described in detail herein, the beads are coated with an antibody to an analyte in said sample, which provides the basis for an immunoassay. In preferred embodiments, a system comprising a reading apparatus or reader and a single-use cartridge containing the magnetic immunosensor and all the other assay components is used to analyze an analyte in a biological sample.

A. High-Field Magnet

In certain embodiments of the invention, the magnetic immunosensor comprises a sensing electrode on a substantially planar chip and has a high-field magnet, e.g., a permanent magnet or an electromagnet, positioned proximate to (e.g., below) or associated with the chip. The magnetic immunosensor of the present invention provides a field of greater than about 0.1 Tesla and has an "event horizon" (as defined herein) that can efficiently draw beads from a range of about 0.05 mm to about 5 mm in the region of the sensing electrode.

The high-field magnet, e.g., permanent magnet or electromagnet, of the present invention includes any material that provides a high magnetic field (e.g., greater than about 0.1 Tesla, greater than 0.4 Tesla or greater than 1 Tesla). The magnetic field can be measured, for example, as the remnant field on a substantially flat surface area of a magnet. While the preferred material is a neodymium iron boron alloy (NdFeB) alloy, and more preferably $Nd_2Fe_{14}B$, other materials may be used. For example, those skilled in the art will recognize that high-field permanent magnets can include ferrite or aluminum nickel cobalt (AlNiCo) magnets, which typically exhibit fields of 0.1 to 1 Tesla. Other high-field permanent magnets comprised of alloys of rare earth elements (e.g., neodymium alloys and samarium cobalt (SmCo) alloys) exhibit fields in excess of 1 Tesla, e.g., greater than 1.2 Tesla or greater than 1.4 Tesla.

Rare earth magnets are generally brittle and also vulnerable to corrosion, and as such these materials are frequently plated or coated to protect them from breaking and chipping. In addition, the Curie point of rare earth magnets is substantially above the temperatures encountered in the immunoassay of the present invention, which may be run in the ambient to about 50° C. range, typically thermostated at 37° C. for assays in blood.

As used herein, "Curie point" or "Curie temperature" refers to a characteristic property of a ferromagnetic material. The Curie point of a ferromagnetic material is the temperature above which it loses its characteristic ferromagnetic ability to possess a net (spontaneous) magnetization in the absence of an external magnetic field. At temperatures below the Curie point, the magnetic moments are partially aligned within magnetic domains in ferromagnetic materials. As the temperature is increased from below the Curie point, thermal fluctuations increasingly destroy this alignment, until the net magnetization becomes zero at and above the Curie point. Above the Curie point, the material is purely paramagnetic.

In another embodiment, the high-field magnet comprises an electromagnet in which the magnetic field is produced by the flow of electric current. The electric current may be provided by a reader, in which the immunosensing device is inserted and with which the immunosensing device is in electrical contact.

1. Bulk Magnet Positioned in Housing of Magnetic Immunosensor

The magnetic immunosensor of some embodiments of the invention comprises a sensing electrode on a substantially planar chip and a bulk permanent high-field magnet positioned proximate to the electrode (e.g., below or on the opposite side of the chip). In certain preferred embodiments, the bulk permanent high-field magnet is positioned in the housing (e.g., cut out or trench in the plastic cartridge) of the magnetic immunosensing device. Preferably, the bulk permanent high-field magnet is positioned within the base of the plastic cartridge housing (e.g., non-coplanar with the sensing electrode). In other embodiments, the magnet is positioned adjacent to or within the reading apparatus or reader of the immunosensing device.

In one embodiment, the bulk high-field permanent magnet is substantially cylindrical, having a diameter in the range of about 0.1 mm to about 5 mm and a length of about 0.1 mm to about 5 mm, and is positioned to yield an "event horizon" (as defined herein) in the conduit suitable for bead capture within a short period of time (e.g., 1-5 minutes). The conduit generally has a height of about 0.2 mm to about 5 mm and a width of about 0.2 mm to about 5 mm, and either a uniform or non-uniform cross-sectional area. In other embodiments, the bulk magnet shape may be in the form of a square, rectangle, oval, flake, pyramid, sphere, sub-sphere, or other shaped form.

The method of some embodiments of the invention includes (a) mixing magnetically susceptible beads coated with a capture antibody with a sample suspected of containing an analyte, and a signal antibody to form a sandwich on the beads, (b) applying the mixture to the immunosensor and magnetically localizing and retaining at least a portion of the beads on the immunosensor, (c) washing the unbound sample from the immunosensor, and (d) exposing the signal antibody of the sandwich to a signal generating reagent, and measuring a signal from the reagent at the electrode. In some embodiments, the method can use magnetically susceptible beads and signal antibodies dissolved from a dry matrix. In other embodiments, the method operationally relies on step (a) occurring in a first portion of a conduit and step (b) occurring in a second portion of a conduit where the sensor is located.

2. Magnetized Layer Integral to Magnetic Immunosensing Device

Another embodiment of the present invention includes a magnetic immunosensing device, which comprises a sensing electrode on a substantially planar chip. The electrode is positioned in a conduit for receiving a sample mixed with antibody-labeled magnetically susceptible beads and a magnetized layer (e.g., microfabricated magnetic layer). The magnetized layer may be included on (e.g., positioned over, directly attached, coated or patterned onto any surface of the chip) or embedded into the chip (e.g., positioned within the chip, integral to the chip). This configuration attracts the magnetically susceptible beads substantially proximate to the electrode and substantially retains them at the electrode during removal of unbound sample and washing of the electrode.

The magnetized layer preferably is formed from a mobile magnetic composition, e.g., a slurry, comprising a material capable of sustaining a high-field permanent magnetic field, e.g., a NdFeB alloy, as particles in an immobilization or support matrix (e.g., a polyimide, polyvinyl alcohol (PVA) or thermoplastic equivalent). This slurry is not limited by viscosity and can include any viscosity suitable for application. In various optional embodiments, the mobile magnetic composition has a viscosity ranging from 0.3 to 300,000 CPS, e.g., from 100 to 100,000 CPS or from 1,000 to 10,000 CPS. The magnetic particles in the slurry of certain embodiments of the invention have an average particle size from 0.01 μm to 100 μm, e.g., from 0.1 μm to 10 μm or from 3 μm to 7 μm.

In addition to polyimide, PVA and thermoplastic polyimide, two-part chemically cured epoxy resins, kapton and the like may be used as the support matrix for fixing the magnetic particles to the wafer. The methods of curing the matrix may be based on a photo-initiated, thermally initiated or chemically initiated process. In certain embodiments, the immobilization matrix is comprised of other photoformed matrix materials.

As provided above, the slurry can be applied in a variety of locations in or on the immunosensing device (e.g., to the front side or backside of a wafer or chip, electrode, housing, reader, etc.). For example, in some embodiments of the invention, the high-field permanent magnetic material is applied to the substantially planar chip in a patterned manner (e.g., using a mask). In certain embodiments, the high-field permanent magnetic material is also applied to a microfabricated sensing electrode. In other embodiments, the slurry is applied in a layer below the sensing electrode.

Prior to the application process, the slurry may or may not be magnetized. However, after the deposition step, the magnetic layer preferably is magnetized to provide directionality to the field.

B. Sensing Electrode

The sensing electrode is preferably microfabricated (e.g., an amperometric gold array) on a substantially planar chip (e.g., silicon wafer), as described in the jointly-owned pending and issued patents cited herein (e.g., U.S. Pat. Nos. 5,200,051 and 7,419,821).

C. Magnetically Susceptible Beads

In various embodiments of the invention, the biological sample, e.g., blood sample, is amended with magnetically susceptible beads. The magnetically susceptible beads may be comprised of any material known in the art that is susceptive to movement by a magnet (e.g., permanent magnet or electromagnet) utilized in or in concert with the device of the present invention. As such, the terms "magnetic" and "magnetically susceptible" with regard to beads can be used interchangeably.

In some embodiments of the invention, the beads include a magnetic core, which preferably is completely or partially coated with a coating material. The magnetic core may comprise a ferromagnetic, paramagnetic or a superparamagnetic material. In preferred embodiments, the magnetically susceptible beads comprise a ferrite core and an outer polymer coating. However, the magnetic core may comprise one or more of Fe, Co, Mn, Ni, metals comprising one or more of these elements, ordered alloys of these elements, crystals comprised of these elements, magnetic oxide structures, such as ferrites, and combinations thereof. In other embodiments, the magnetic core may be comprised of magnetite ($Fe_3O_4$), maghemite ($\gamma$-$Fe_2O_3$), or divalent metal-ferrites provided by the formula $Me_{1-x}OFe_3+xO_3$ where Me is, for example, Cu, Fe, Ni, Co, Mn, Mg, or Zn or combinations of these materials, and where x ranges from 0.01 to 99.

Suitable materials for the coating include synthetic and biological polymers, copolymers and polymer blends, and inorganic materials. Polymer materials may include various combinations of polymers of acrylates, siloxanes, styrenes, acetates, alkylene glycols, alkylenes, alkylene oxides, parylenes, lactic acid, and glycolic acid. Biopolymer materials include starch or similar carbohydrate. Inorganic coating materials may include any combination of a metal, a metal alloy, and a ceramic. Examples of ceramic materials may include hydroxyapatite, silicon carbide, carboxylate, sulfonate, phosphate, ferrite, phosphonate, and oxides of Group IV elements of the Periodic Table of Elements.

In other embodiments of the invention, the magnetic beads comprise non-magnetic substrate beads formed, for example, of a material selected from the group consisting of polystyrene, polyacrylic acid and dextran, upon which a magnetic coating is placed.

In principal, any correctly-sized magnetically susceptible bead capable of being positioned with the high-field magnet of the present invention may be utilized, taking into account the dispersability requirements for the magnetically susceptible beads. In preferred embodiments, at least 50 wt. %, e.g., at least 75 wt. %, of the magnetically susceptible beads are retained at the electrode surface. In some exemplary embodiments, the average particle size of the magnetically susceptible beads may range from 0.01 µm to 20 µm, e.g., from 0.1 µm to 10 µm, from 0.1 µm to 5 µm or from 0.2 µm to 1.5 µm. As used herein, the term "average particle size" refers to the average longest dimension of the particles, e.g., beads, for example the diameter for spherical particles, as determined by methods well-known in the art. The particle size distribution of the magnetically susceptible beads preferably is unimodal, although polymodal distributions may also be used in accordance with the present invention. While use of a spherical magnetically susceptible bead is preferred, in other embodiments, other bead shapes and structures, e.g., ovals, sub-spherical, cylindrical and other irregular shaped particles, are within the meaning of the term "beads" and "microparticles" as used herein.

Commercial sources for magnetically susceptible bead preparations include Invitrogen™ (Carlsbad, Calif., U.S.A.) by Life Technologies™, Ademtech (Pessac, France), Chemicell GmbH (Berlin, Germany), Bangs Laboratories, Inc.™ (Fishers, Ind.) and Seradyn, Inc. (Indianapolis, Ind.). Many of the commercially available products incorporate surface functionalization that can be employed to immobilize antibodies (e.g., IgG) on the bead surfaces. Exemplary functionalizations include carboxyl, amino or streptavidin-modified magnetically susceptible beads.

The magnetically susceptible beads are preferably coated with an antibody to an analyte that is a cardiovascular marker, e.g., cardiac troponin I, troponin T, a troponin complex, human chorionic gonadotropin, BNP, creatine kinase, creatine kinase subunit M, creatine kinase subunit B, creatine kinase MB (CK-MB), proBNP, NT-proBNP, myoglobin, myosin light chain or modified fragments thereof, among others. In addition, markers for other indications can be utilized. Further exemplary analytes include, but are not limited to, beta-HCG, TSH, ultra hTSH II, TT3, TT4, FT3, F14, myeloperoxidase, D-dimer, CRP, NGAL, PSA, LH, FSH, galectin-3, prolactin, progesterone, estradiol, DHEA-S, AFP, CA 125 II, CA 125, CA 15-3, CA 19-9, CA 19-9XR, CEA, thyroxine (T4), triiodothyronine (T3), T-uptake, Tg, anti-Tg, anti-TPO, ferritin, cortisol, insulin, HBsAg, HCV Ag/Ab combo, HCV core Ag, anti-HCV, AUSAB (anti-HBs), CORE, CORE-M, SHBG, iPTH, theophylline, sirolimus, tacrolimus, anti-HAV, anti-HAV IgM, HAVAB, HAVAB-M, HAVAB-M2.0, HAVAB-G, HAVAB 2.0, HAVAB 2.0 Quant, IgM, CMV IgM, CMV IgG, â-2-microglobulin, digitoxin, HBe, anti-HBe, HBeAg, HIV ½gO, HIV Ag/Ab combo, testosterone, SCC, vitamin B12, folate, syphilis, anti-HBc, rubella IgG, rubella IgM, homocysteine, MPO, cytomegalovirus (CMV) IgG Avidity, toxo IgG avidity, toxo IgG, toxo IgM, C-peptide, vitamin D, HTLV I/II, total âhCG, progesterone, estradrogen, prolactin, myoglobin, tPSA, fPSA, carbamazepine (CBZ), digoxin, gentamicin, NAPA, phenyloin, phenobarbital, valproic acid, vancomycin, procaine, quinidine, tobramycin, methamphetamine (METH), amphetamine (AMPH), barbituates, benzodiazepine, cannabis, cocaine, methadone, opiates, PCP, acetaminophen, ethanol, salicylates, tricyclics, holoTc, anti-CCP, HbA1c, barbs-U, among others. In certain embodiments of the invention, the antibody is to a low-abundance analyte in the sample. Abbreviated names above will be familiar to one of ordinary skill in the clinical analytical art.

The magnetic immunosensor and methods of the present invention preferably also comprise a second antibody, which is a labeled antibody, also referred to herein as a signal antibody. In some embodiments, the labeled antibody is in the form of a dissolvable dry reagent, which also may comprise the magnetically susceptible beads that are employed in the present invention, as discussed below. Both the immobilized and labeled antibodies can be monoclonal, polyclonal, fragments thereof and combinations thereof. In addition, one or more of the antibodies can be labeled with various labels including a radiolabel, enzyme, chromophore, fluorophore, chemiluminescent species, ionophore, electroactive species and others known in the immunoassay art. Where the second antibody is labeled with an enzyme, it is preferably ALP, horseradish peroxidase, or glucose oxidase. In other embodiments, the analyte is labeled with fluorescein, ferrocene, p-aminophenol, or derivatives thereof.

In certain embodiments, the magnetically susceptible beads are deposited in a suitable region of the magnetic immunosensing device as a suspension in, for example, a mixture of lactitol and DEAE-dextran such as that supplied by Advanced Enzyme Technologies (Pontypool, Great Britain). Evaporation of the solvent, usually water, yields a glassy deposit in which the beads are immobilized. The lactitol/DEAE-dextran allows the beads to be regionalized within the device in a mechanically and biochemically stable state, but which also rapidly dissolves upon contact with a sample.

In other embodiments, the magnetically susceptible beads are homogeneously mixed with the sample. In still other embodiments, the magnetically susceptible beads may be less homogeneously mixed with the sample; however, the intent is to optimize the position and concentration of the beads relative to the sensing electrode. Those skilled in the art will recognize that the magnetically susceptible beads of the present invention may be added to the biological sample prior to introduction into the magnetic immunosensing device, such as, for example, as an integral part of a blood collection device or as a standard manual addition step. However, for the convenience of the user and to assure a quality assay, the magnetically susceptible beads are preferably included within the device.

In some embodiments of the invention, the sample, e.g., whole blood sample, is collected and then amended by dissolving a dry reagent comprising the magnetically susceptible beads into the sample. Any portion of the immunosensing device may be coated with the dry reagent (e.g., sensing device, conduit, sample entry port, sample holding chamber). In addition to the magnetically susceptible beads, the dry reagent may further include one or more of: beads for reducing leukocyte interference, a leukocidal reagent, buffer, salt, surfactant, stabilizing agent, simple carbohydrate, complex carbohydrate and various combinations thereof. The dry reagent can also include an enzyme-labeled antibody (e.g., the above-described labeled antibody) to the analyte.

In various embodiments, the magnetically susceptible beads are used to amend the biological sample, e.g., blood, in a first container or location, and then the sample is passed to a second container or location that includes the capture and signal antibodies. In some embodiments, the magnetically susceptible beads are contained in solution and mixed with the biological sample, and the resulting amended sample is introduced into the magnetic immunosensing device. For example, a blood sample may be mixed with the magnetically susceptible beads to form an amended sample, which is then introduced into the device. In certain embodiments, the magnetic immunosensing device, e.g., cartridge, includes a pouch that contains a liquid comprising the magnetically susceptible beads, which may be mixed with a biological sample in the device and then processed substantially as described herein to form an assay (e.g., sandwich assay) for analyte detection.

In other embodiments, electrowetting is employed to mix a first liquid comprising the magnetically susceptible beads with a liquid biological sample, e.g., blood. In one such embodiment, an apparatus may be provided for manipulating droplets. The apparatus, for example, may have a single-sided electrode design in which all conductive elements are contained on one surface on which droplets are manipulated. In other embodiments, an additional surface is provided parallel with the first surface for the purpose of containing the droplets to be manipulated. The droplets are manipulated by performing electrowetting-based techniques in which electrodes contained on or embedded in the first surface are sequentially energized and de-energized in a controlled manner. The apparatus may allow for a number of droplet manipulation processes, including merging and mixing two droplets together, splitting a droplet into two or more droplets, sampling a continuous liquid flow by forming from the flow individually controllable droplets, and iterative binary or digital mixing of droplets to obtain a desired mixing ratio.

In addition, any immunoassay format known in the art may be modified to include the magnetically susceptible beads of the present invention, for example, by adding the beads in a sample pre-treatment step. The pretreatment may be accomplished, for example, by incorporating the beads in a blood collection device, in a separate vessel, or may take place in the immunoassay device itself by incorporation of the beads in the test cycle of the device.

In various embodiments of the invention, the beads are mobile and thereby capable of interacting with an analyte. After binding to the analyte of interest, magnetic forces are used to concentrate the beads at the electrode for measurement causing the magnetically susceptible beads to be localized to the amperometric electrode for signal detection. One advantage of using mobile beads according to the present invention is that their motion in the sample or fluid accelerates binding reactions, making the capture step of the assay faster.

D. Additives

In some embodiments of the invention, additives may be included in the magnetic immunosensing device or used in conjunction with the assay. In certain embodiments, an anticoagulant can be added. For example, heparin may be added to improve performance in cases where the sample was not collected in a heparinized tube or was not properly mixed in a heparinized tube. A sufficient amount of heparin may be added so that fresh unheparinized blood will remain uncoagulated during the assay cycle of the cartridge, typically in the range of 2 to 20 minutes. In still other embodiments, one or more of proclin, DEAE-dextran, tris buffer, and lactitol can be added as reagent stabilizers. In further embodiments, a surfactant such as polysorbate 20, also known as Tween® 20, can be added to reduce binding of proteins to plastic, which is a preferred material for the cartridge housing of the magnetic immunosensing device. The addition of a surfactant also facilitates the even coating of reagents on plastic surfaces and minimizes the crystallization of sugars (e.g., lactitol). In other embodiments of the invention, an antibacterial agent or biocide (e.g., sodium azide) may be added to inhibit bacterial growth.

II. Manufacture of Magnetic Immunosensing Device

In one embodiment of the invention, a silicon wafer is thermally oxidized to form an insulating oxide layer having a thickness of about 1 µm. A titanium/tungsten layer is then sputtered onto the oxide layer to a preferable thickness of about 100 Å to about 1000 Å, followed by a layer of gold that is from 500 Å to 1000 Å thick, most preferably about 800 Å thick. Next, a photoresist is spun onto the wafer and is dried and baked. The surface is then exposed using a contact mask, the latent image is developed, and the wafer is exposed to a gold-etchant. The patterned gold layer is coated with a photodefinable polyimide, suitably baked, exposed using a contact mask, developed, cleaned in an oxygen plasma, and preferably imidized at 350° C. for about 5 hours. This leaves a large number of electrode openings in the polyimide layer in a square array. In some embodiments, the square array has a diameter, for example, from 2 µm to 100 µm, from 5 µm to 15 µm or about 7 µm, with an inter-distance of, for example, from 5 µm to 100 µm, from 10 µm to 20 µm or about 15 µm. The area covered by these electrodes (i.e., sensor area) is substantially circular with a diameter of, for example, from 50 µm to 1000 µm, from 100 µm to 300 µm or about 300 µm.

After dicing the wafer into individual chips, each chip is assembled into a single-use cartridge. The cartridges may be of the type described in U.S. Pat. No. 7,419,821 to Davis et al. or jointly-owned U.S. Patent Application No. 61/288,189, entitled "Foldable Cartridge Housings for Sample Analysis," filed Dec. 18, 2009, the entireties of which are incorporated herein by reference. In one embodiment, the sensor is positioned in a conduit for receiving a sample, and a high-field magnet, e.g., permanent or electromagnet, is positioned directly below the sensor, preferably in the center region thereof. In another embodiment, a high-field magnet can be positioned above the sensor region of the conduit. These elements may be in a fixed position within the instrument housing, or adapted to an actuator capable of moving in and out of position with respect to the immunosensor and conduit. The one or more high-field magnets can be used for attracting magnetically susceptible beads in the conduit (e.g., substantially proximate to the sensor) and retaining them in the region of the sensor during removal of sample and washing of the sensor to remove unbound or partially absorbed reagents. As described above, the magnetic beads are coated with an antibody to an analyte that may be present in the sample.

A. Trenches

In the immunosensor embodiment of the invention shown in FIG. 1, additional features are depicted. In particular, the cross-sectional representation of FIG. 1 shows an electrochemical sensor patterned in suitable material (e.g., photoformable polyimide) with trenches (or grooves) having width of from about 1 µm to about 100 µm, e.g., from 3 µm to 50 µm or from 10 µm to 20 µm, height or depth of from about 0.1 µm to about 100 µm, e.g., from 1 µm to 50 µm or from 5 µm to 10 µm, and length of about 1 µm to about 5000 µm, e.g., from 10 µm to 1000 µm or from 100 µm to 500 µm. In this immunosensor design embodiment, the planar chip is positioned into an analytical system capable of applying magnetic fields in either direction in roughly the z axis, as shown by vectors B1 and B2. In some embodiments and as shown in FIG. 1, the trenches may be oriented in a direction substantially parallel to the direction of sample flow in the immunosensing device. In alternative embodiments, the trenches may be oriented in a direction substantially transverse to or perpendicular to the direction of sample flow. The trench structure of the present invention may beneficially inhibit fluid motion in the x and/or y directions from removing any magnetically susceptible beads that have been magnetically localized within a trench, for example, by a washing fluid.

Figure 2:
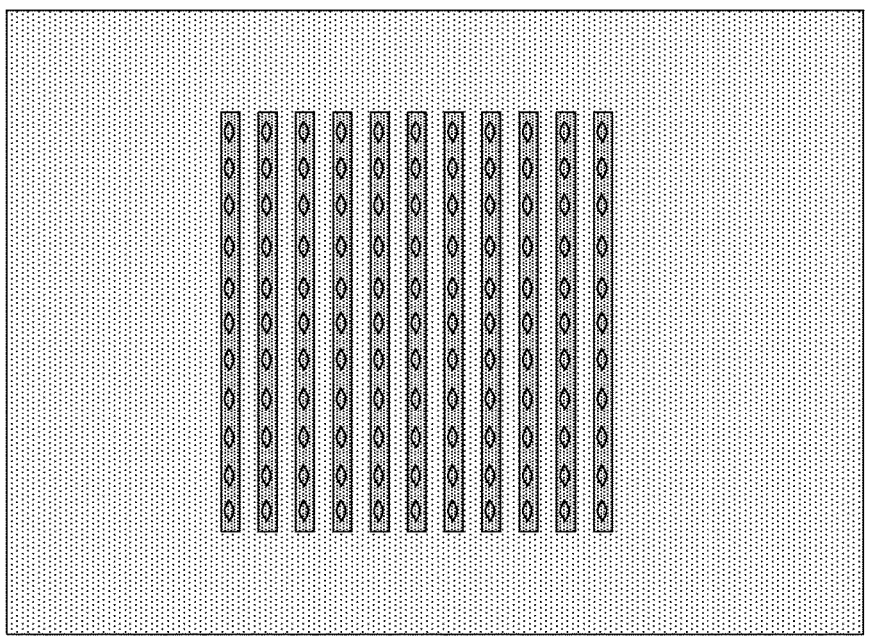
FIG. 2 is a top view of the grooved immunosensor chip and a microelectrode array.

A top view illustration of the electrochemical sensor of FIG. 1 is illustrated in FIG. 2, in which microelectrodes of diameter µD (i.e., about 1 µm to about 100 µm) and spacing µL (about 5 µm to about 500 µm) are observed at the bottom of each groove in the sensor structure as an array. These microelectrodes can be comprised of gold or other suitable conductor and can be patterned as described above (e.g., with gold and polyimide). In preferred embodiments, the high-field magnet is positioned on the underside or below the electrochemical sensor.

B. Magnetic Fields

In some embodiments of the invention, a sandwich immunoassay is formed on the magnetically susceptible beads substantially everywhere in the conduit and the beads are slowly collected on or adjacent to a sensor surface by bringing the magnet proximal to the cartridge and slowly oscillating the fluid. In certain embodiments, the oscillating magnetic fields are produced by a moveable high-field magnet, e.g., permanent magnet or electromagnet, located inside the instrument. In other embodiments, one or more magnets are stationary inside the instrument and the sandwich formation is located in a position beyond the field. The sample may then be directed, e.g., by a pump or similar means, into a region where the magnetic field is sufficiently strong for capture.

In a preferred embodiment, the sample is oscillated in a back and forth motion over the sensor, e.g., by one or more pumps, while the magnetic field is applied, in order to maximize the opportunity for the magnetically susceptible beads to be attracted to the sensor surface.

III. Methods of Performing Immunoassays

The present invention is applicable to methods of performing immunoassays with a magnetic immunosensor. In preferred embodiments, the present invention may be employed in one or more of the following areas: immunosensors, most notably in the context of point-of-care testing; electrochemical immunoassays; immunosensors in conjunction with immuno-reference sensors; whole blood immunoassays; single-use cartridge based immunoassays; and non-sequential immunoassays with only a single wash step; and dry reagent coatings. As will be appreciated by those skilled in the art, the general concept disclosed herein is applicable to many immunoassay methods and platforms.

The methods of the invention are applicable to various biological sample types (e.g., blood, plasma, serum, urine, interstitial fluid and cerebrospinal fluid). The present invention is applicable a variety of immunoassays including both sandwich and competitive immunoassays.

A. Sandwich Immunoassay

In sandwich assay embodiments, the sample contacts the immunosensor with an immobilized first antibody to the target analyte, and a labeled second antibody to said target analyte. In some embodiments of the invention, the sample, e.g., whole blood sample, is collected and then amended by dissolving a dry reagent comprising magnetically susceptible beads into the sample. As discussed above, the beads preferably include an antibody to the analyte of interest immobilized on the outer surface thereof. The dissolution of the dry reagents and the sandwich formation step can occur concurrently or in a stepwise manner.

The magnetically susceptible bead concentration employed may vary widely. In some exemplary embodiments, the sample is amended with the magnetically susceptible beads to provide a dissolved bead concentration of at least 5 µg per µL of sample, e.g., at least 10 µg per µL of sample, or at least 15 µg per µL of sample. The dry reagent preferably dissolves into the sample to give a bead concentration of from about 5 µg to about 40 µg beads per µL of sample, preferably from about 10 to about 20 µg beads per µL of sample. Depending on the size of the beads, this corresponds to at least about $10^4$ beads per µL of sample, at least about $10^5$ beads per of sample, or approximately from about $10^5$ to about $10^6$ beads per µL of sample. Thus, in some preferred embodiments, the beads are present in an amount sufficient to provide a dissolved bead concentration of at least $10^4$ beads per µL of sample, e.g., at least about $10^5$ beads per µL of sample, or from about $10^5$ to about $10^6$ beads per µL of sample. Once this step is completed, it is possible to perform an immunoassay, e.g., an electrochemical immunoassay, on the amended sample to determine the concentration of an analyte. In preferred embodiments of the invention, at least about 10,000 beads are used for each assay. This lower limit reduces counting error issues, e.g., about 1% or greater for about 1,000 beads or less. Defining an upper limit is less straightforward and depends on bead size, however about 10,000,000 beads is generally sufficient. In certain embodiments, the dissolved bead volume is less than about 1% of the total sample assay volume, and is preferably less than about 0.1%.

In the actual assay step, in preferred embodiments, once the sandwich is formed between the immobilized and signal antibodies on the outer surface of the magnetically susceptible beads, a magnetic field is applied to attract the beads in the conduit substantially proximate to the electrode. The sample is subsequently washed to a waste chamber while leaving the retained beads substantially proximate to the electrode, followed by exposing the sandwich on the magnetically susceptible beads to a substrate capable of reacting with an enzyme to form a product capable of electrochemical detection. One exemplary format is an electrochemical enzyme-linked immunosorbent assay.

In some embodiments of the invention, a magnetized layer (e.g., microfabricated magnetic layer) can be used as the basis for a sandwich immunoassay method. For example, in one embodiment, the invention is to a method of performing an immunoassay with a magnetic immunosensor where the immunosensor comprises a sensing electrode on a substantially planar chip and an additional layer on the chip that is magnetized, positioned in the region of the electrode. This method comprises (a) mixing magnetically susceptible beads coated with a capture antibody with a sample containing (or suspected of containing) an analyte and a signal antibody to form a sandwich on the beads, (b) applying the mixture to the immunosensor and magnetically localizing and retaining at least a portion of the beads on the immunosensor, (c) washing the sample and unbound material from the immunosensor and exposing the signal antibody of the sandwich to a signal generating reagent, and (d) measuring a signal from the reagent at the electrode. Furthermore, step (a) preferably occurs in a first portion of a conduit and step (b) preferably occurs in a second portion of a conduit where the sensor resides. In some embodiments, other features of the assay (e.g., sample type, the use of dry reagents including magnetically susceptible beads and the signal antibodies, as described herein) can be optimized to facilitate the dissolution of a dry matrix into the sample.

B. Competitive Immunoassay

Embodiments of the present invention are also applicable to methods of performing a competitive immunoassay with a magnetic immunosensor. In traditional competitive assay embodiments, a sample contacts an immunosensor comprising an immobilized first antibody to a target analyte, and a labeled target analyte that competes for binding with the target analyte. Because the (unlabeled) target analyte competes with (amended) labeled target analyte, the resulting signal is inversely proportional to the native analyte concentration of the sample.

In some such embodiments, the method of the invention includes mixing magnetically susceptible beads coated with a capture antibody with a sample containing (or suspected of containing) an analyte and an added labeled form of the analyte to permit competitive binding on the magnetically susceptible beads, applying the mixture to an immunosensor and magnetically localizing and retaining at least a portion of the beads on the immunosensor, washing the sample and unbound material from the immunosensor, exposing the labeled analyte to a signal generating reagent, and measuring a signal from the reagent at the sensing electrode.

C. i-STAT® Immunoassay

While the present invention is broadly applicable to immunoassay systems, it is best understood in the context of the i-STAT® immunoassay system (Abbott Point of Care Inc., Princeton, N.J., USA), as described in the jointly-owned pending and issued patents cited herein.

In these immunoassay systems, only a small fraction of analyte present in the sample is captured. The assay involves sampling of an analyte present in plasma or whole blood by capturing analyte on an antibody-labeled microparticle which is coated (or permanently bound) to the surface of a sensor, e.g. an electrochemical sensor. In certain embodiments, a second antibody labeled with an enzyme then binds to the analyte to make a sandwich. The electrochemical detection format ensures that substantially all the enzyme (e.g., alkaline phosphatase (ALP)) is detected (i.e., detection efficiency approaches 100%), which allows for a high sensitivity assay. Typically, however, the overall amount of analyte that is in the region of the antibody-labeled microparticle and susceptible to capture during normal usage is low due to mass transport limitations. It would be advantageous, therefore, to capture a higher percentage of the analyte, while still retaining the high efficiency of the detection step. As disclosed in the present invention, more analyte advantageously may be captured and detected by employing capture of a magnetically susceptible bead reagent that is distributed (e.g., homogeneously distributed) throughout the sample during the analyte capture step, but is magnetically localized to the sensor in such a way that retains the ability to measure the enzyme with sufficiently improved detection efficiency.

In certain embodiments, the sample, e.g., plasma or whole blood sample, is amended with interference-reducing and/or conditioning reagents optionally located in a sample inlet print of a cartridge. For example, the reagents may contain immunoglobulins, immunoglobulin-coated non-magnetically susceptible beads, non-magnetically susceptible bead reagents for interference screening, and other stabilizing or conditioning reagents. See, e.g., U.S. Publication Nos. 2011/0117581 and 2011/0117580, each of which is incorporated herein by reference in its entirety, for a description of the use of sacrificial beads for reducing or eliminating interference caused by leukocytes in a blood sample. See also U.S. Publication No. 2010/0248273, the entirety of which is incorporated herein by reference, which describes the use of non-human IgM and/or IgG or fragments thereof to reduce interference caused by heterophile antibodies.

Upon being pushed into a conduit, the sample is amended with at least two reagents, a primary capture reagent and a labeled conjugate reagent. The primary capture reagent comprises magnetically susceptible beads coated with antibodies or antibody fragments appropriate to the analyte of interest. This magnetically susceptible bead reagent may be printed, for example, on a wall portion of the holding chamber or attached to a conduit in a region upstream of the sensor chip, using methods described in jointly-owned U.S. Pat. No. 5,554,339 to Cozzette et al., which is hereby incorporated by reference in its entirety. The labeled conjugate reagent preferably also comprises a signaling element (e.g., ALP). This reagent may be printed, for example, as a dissolvable matrix with the primary capture reagent in a one stage assay. In another embodiment, the two reagents are amended into the sample separately from one another, in either order.

To promote sandwich formation on the magnetically susceptible beads, it is desirable that the amended sample be oscillated or mixed in the conduit for an appropriate period of time (e.g., about 1 minute to about 20 minutes or about 5 to 10 minutes). This allows analyte present in the sample to be captured on the surface of the beads and labeled with a signal-generating conjugate.

In one embodiment, following capture, magnetic field B1 is applied in such a way that the magnetically susceptible beads are induced to migrate to the top of the sensor channel, opposite the sensor surface, where they are temporarily retained. The surface (i.e., top of sensor channel) may be patterned in such a way that there is a tendency of the beads to resist (beyond the action of B1) movement in the direction of mixing upon subsequent fluid movement. This process can be accompanied by low-amplitude oscillations in the direction of the capture motion (x-axis) in order to assist capture of the magnetically susceptible beads without entrapping formed elements or non-magnetically susceptible beads.

In one embodiment, the sample is then moved to a waste chamber. However, in a preferred embodiment, the sample is moved to a lock-wick feature by means of pressurization actuated by an air-bladder as described in jointly-owned U.S. Pat. No. 7,419,821 to Davis et al. (referenced above) and U.S. Pat. No. 7,723,099 to Miller et al. (referenced above). Each of these patents is hereby incorporated by reference in its entirety.

The movement of the magnetically susceptible beads is conducted in such a way that the magnetic field B1 is able to temporarily retain the beads at the ceiling of the sensor channel, preferably substantially opposite the sensor. During this period, the sensor channel is washed in a fashion similar to that described in U.S. Pat. Nos. 7,419,821 and 7,723,099 (referenced above). In preferred embodiments, prior to completion of the washing step, a portion of the wash fluid is left in the sensor channel until completion of the following magnetic actuation step. In this embodiment, the magnetic field B1 is reversed to B2 with the effect that the beads formerly held in position at the sensor channel ceiling now migrate towards the trenches or grooved sensor structure. Low amplitude oscillations of the fluid portion in the direction of capture mixing can be applied in order to help settle the beads into the trenches of the immunosensor. Upon completion of this step, the wash fluid is slowly pulled from the sensor channel and optionally the magnetic field B2 is turned off. A current arising from the diffusion of an electroactive species generated by the action of bound label on a suitable electrogenic substrate contained in the wash fluid is then measured. (See, for example, U.S. Pat. Nos. 7,419, 821 and 7,723,099 (referenced above)).

As described above, the trenches or grooved structure of the immunosensor are intended to aid capture of the magnetically susceptible beads and yet allow for efficient washing in the direction of fluid movement. However, other suitable structures may also be used. One exemplary structure includes a grid (e.g., rectilinear) array. In this embodiment, the ability to retain the beads over the array will generally depend on the ability to focus magnetic fields in such a way that highest field densities are contained within the area demarcated by the area of the array.

In some embodiments, it is desirable to seek to capture substantially all or a reliable fraction (e.g., over 75 wt. %) of the beads, in which case the dimensions of the bead retention feature (e.g., trenches) are of secondary importance provided that they supply sufficient volume to contain the beads. Alternatively, a fixed proportion of the beads may be sampled in which case the total volume of the capture feature(s) must be held constant. Certain embodiments of the invention utilize sequential application of two opposing magnetic fields. In other embodiments, a single applied field may be utilized. Furthermore, in some embodiments, the ability to provide sufficient substrate to the enzyme-limited detection reaction may require high substrate concentrations (e.g., about 20 mM).

The number and dimensions of the optional trenches or other retention features are dependent on the size and number of the magnetically susceptible beads required to achieve efficient capture of analyte present in the sample. In some embodiments, the length of the trenches, for example, may be several thousand microns while the height and width may be on the order of several microns. In addition, one function of the trenches is to allow for localization and consolidation of the beads and enhanced resistance against fluid motion to dislodge them. In certain embodiments, the beads inside the trenches are mobile.

In other embodiments, after dicing the wafer into individual chips, each chip preferably is assembled into a single-use cartridge and in this example a standard immunosensor is used without the groove features. The sensor is positioned in a conduit for receiving a sample, wherein a single high-field magnet, e.g., permanent magnet or electromagnet, preferably a neodymium iron boron magnet (e.g., $Nd_2Fe_{14}B$), is also positioned directly below the center of the sensor. The high-field magnet is used for attracting magnetically susceptible beads in the conduit (e.g., substantially proximate to the sensor) and retaining them in the region of the sensor during removal of sample and washing of the sensor. In preferred embodiments, the beads are coated with an antibody to an analyte in the sample or suspected of being present in the sample.

Figure 3A:
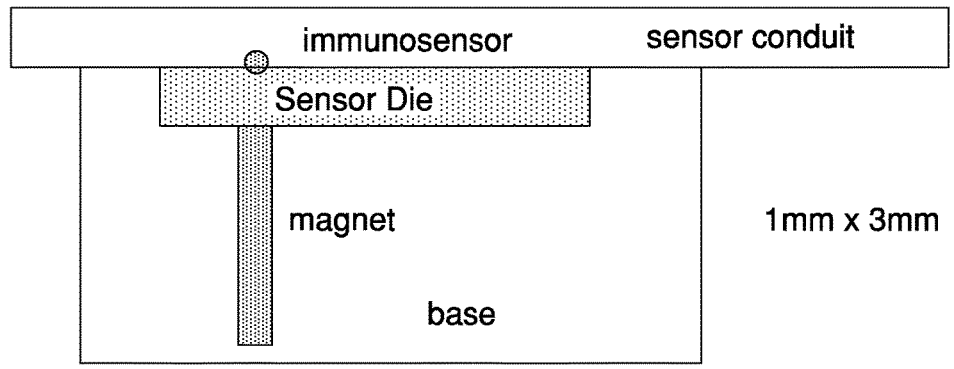
FIGS. 3A-C illustrate various exemplary configurations for the positioning of a rare earth permanent magnet below an immunosensor chip within a cartridge.
Figure 3B:
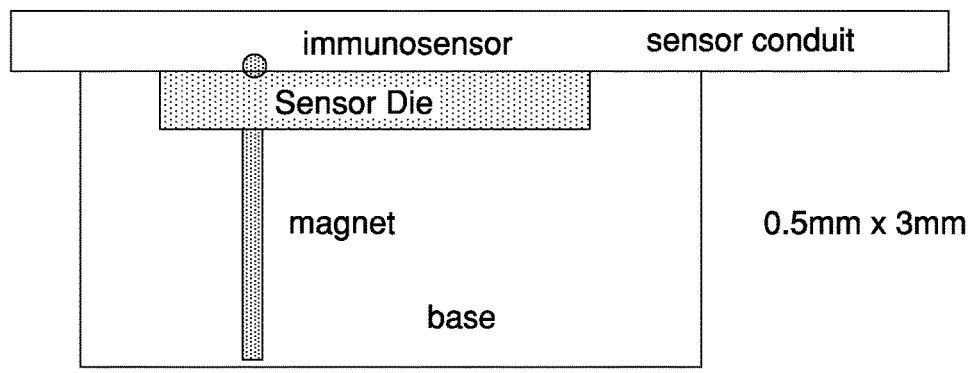
Figure 3C:
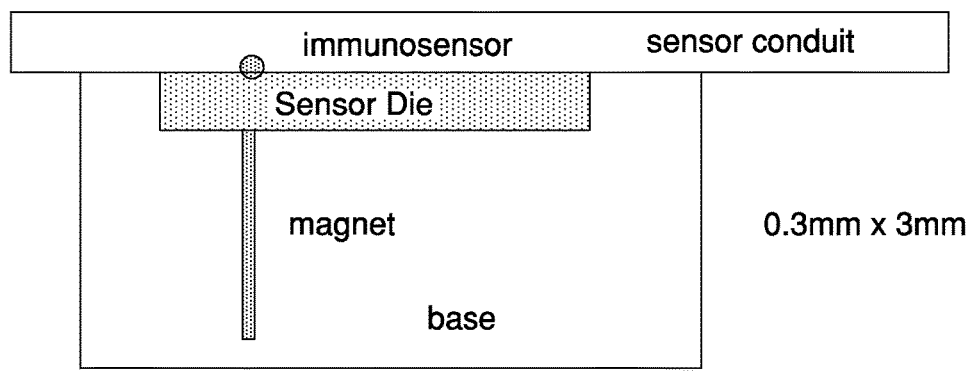

FIGS. 3A-C shows three exemplary configurations of the sensor chip or die in a base or cartridge housing of the type described in jointly-owned U.S. Pat. Nos. 7,419,821 and 7,723,099 (referenced above) or U.S. Patent Application No. 61/288,189 (referenced above). The oval structure on the sensor die corresponds to the immunosensor, which is positioned in the conduit. In each embodiment, the high-field permanent magnets are cylindrical with lengths of from 1 mm to 10 mm, e.g., from 2 mm to 5 mm, preferably about 3 mm, and diameters of from 0.1 mm to 5 mm, e.g., from 0.5 mm to 2 mm. In FIGS. 3A-C, the magnets have diameters of about 1 mm, about 0.5 mm and about 0.3 mm, respectively. The magnets are abutted to the underside of the chip, which preferably has a thickness of from about 0.2 mm to 5 mm, e.g., from 0.5 mm to 2 mm or preferably about 1 mm. FIG. 4 is a schematic representation of the magnetic field lines as the magnet diameter decreases from 1 mm to 0.3 mm and illustrating how the field and magnet selection may impact where on the sensor the magnetically susceptible beads are attracted and focused.

Figure 5:
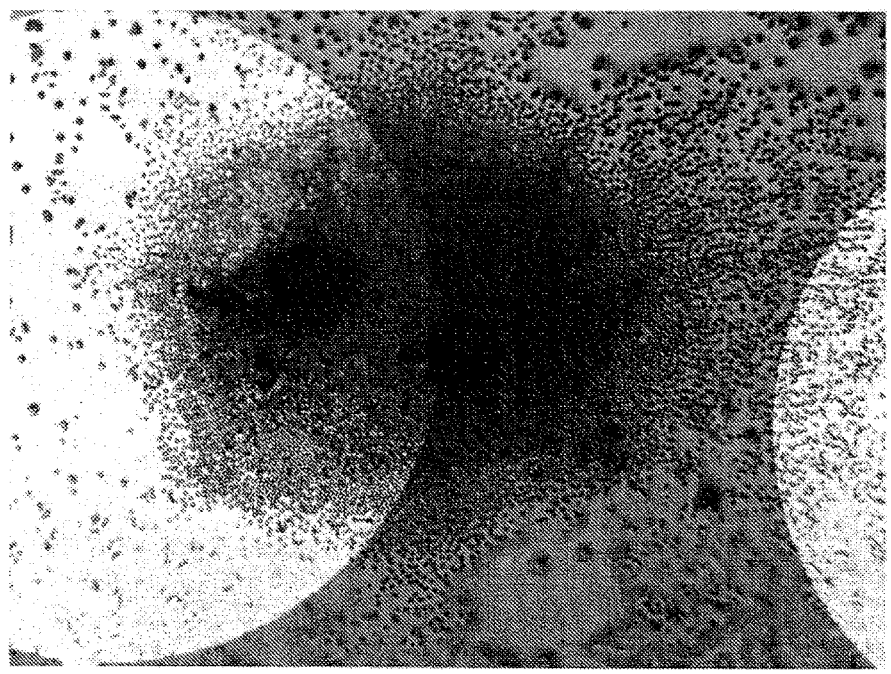
FIG. 5 is a micrograph of magnetically susceptible beads captured on a chip surface where the center of the magnet is positioned directly below the perimeter of an immunosensor.

FIG. 5 is a micrograph of magnetically susceptible beads captured on a chip surface where the center of the magnet having a diameter 1 mm is positioned directly below a point on the perimeter of an immunosensor. This configuration assisted with showing the contrast between beads (black), the gold electrode area (white) and the base silicon material (gray). As shown in FIG. 5, a majority of the beads are localized onto the area of the surface directly above the magnet when a suspension of the beads is passed down the conduit and into the region of the magnet for capture. The beads were about 3 µm in diameter.

Figure 6:
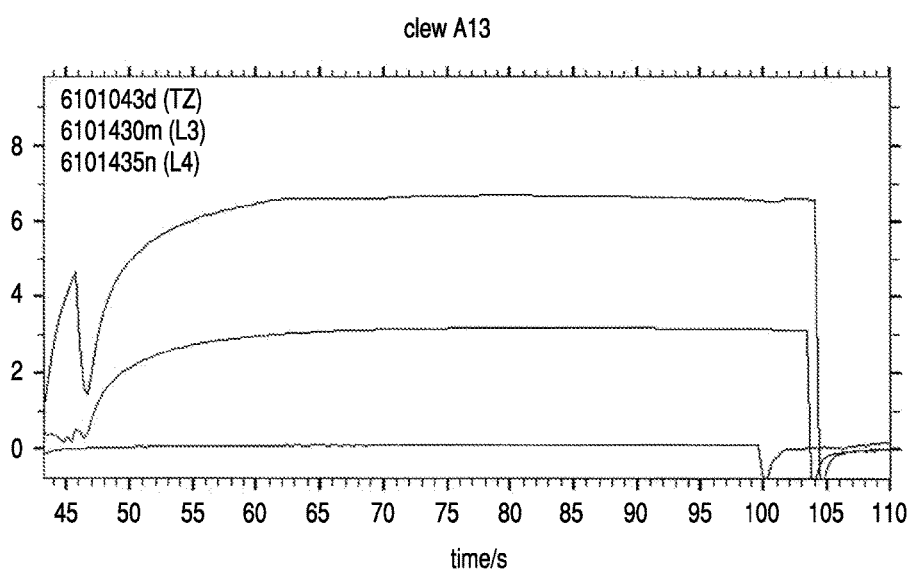
FIG. 6 illustrates three traces of the electrochemical detection step for the magnetically susceptible bead capture assay: plasma with zero cTnI; Cliniqa control level 3; and Cliniqa control level 4.

An immunoassay for cardiac troponin I (cTnI) was performed with a 0.5 mm diameter high-field permanent magnet positioned directly under the center of an immunosensor. Unlike the embodiments using two magnets described above, in this embodiment, the bead sandwich formation step is performed in a portion of the conduit upstream from the sensor, so as to avoid localizing the beads onto the sensor prematurely. FIG. 6 includes three traces of the electrochemical detection step (chronoamperometry) for the magnetically susceptible bead capture assay: plasma with zero cTnI; Cliniqa control level 3; and Cliniqa control level 4. These bitmap curves were run in substantially the same way as a commercial cTnI cartridge, but with special software for the new fluidic motions. All the reagents for this particular experiment were printed on the sensor chip. The cTnI levels L3 and L4 were about 11 ng/mL and 40 ng/mL respectively.

Each trace shows the current at the electrode as a function of time. The rise time of the current to a steady-state value reflects the time constant (TC) for the sensor and the plateau value reflects the amount of analyte in the sample. The traces in FIG. 6 show only the detection step, the complete assay took about 12 minutes, which is acceptable for quantitative point of care immunoassays.

Figure 7:
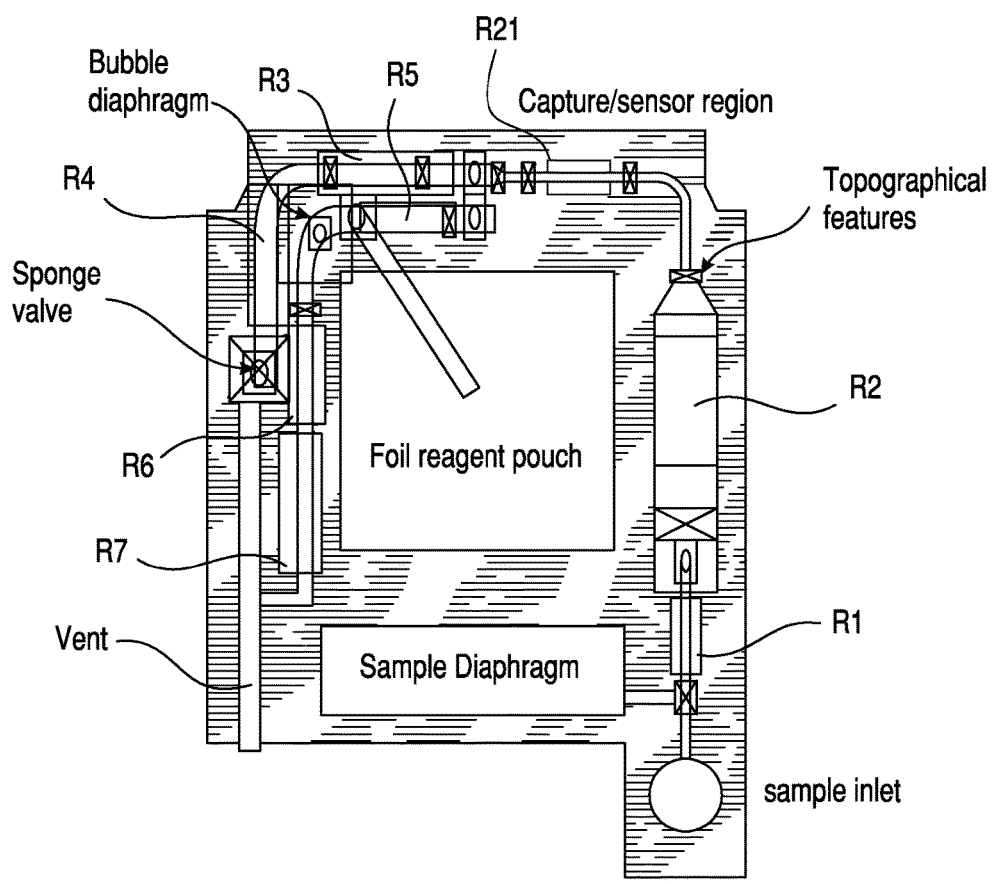
FIG. 7 illustrates the positioning of a rare earth permanent magnet below an immunosensor chip within a cartridge housing in accordance with one embodiment of the present invention.
Figure 8:
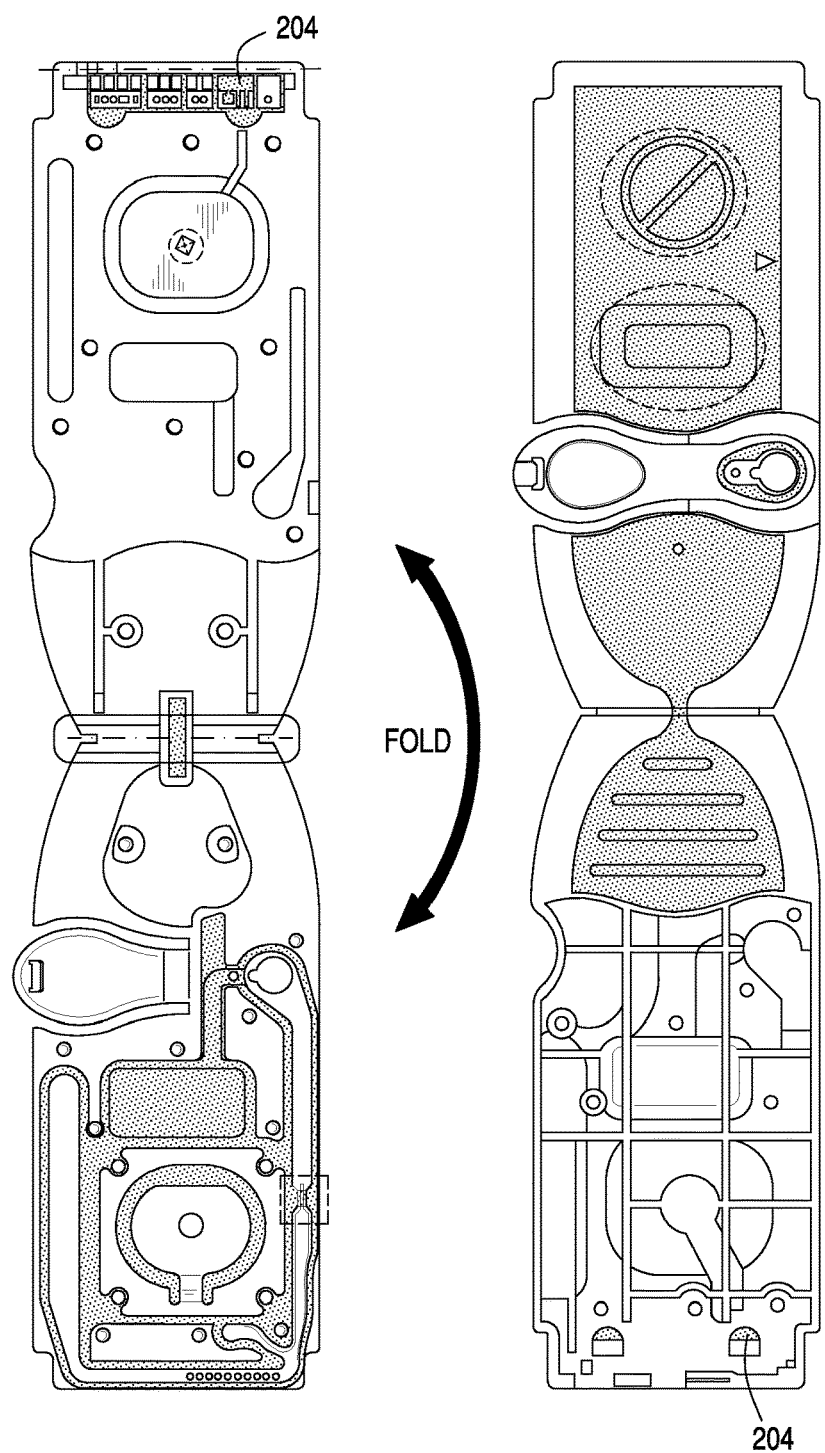
FIG. 8 illustrates a foldable cartridge housing in accordance with one embodiment of the present invention where the rare earth permanent magnet is positioned underneath an immunosensor chip.

Embodiments of the present invention demonstrate that using a fixed permanent magnet in the present device can reliably capture beads (e.g., superparamagnetic or ferromagnetic beads) onto an immunosensor without substantial agglomeration of the beads. In addition, the cartridge fluidic system disclosed in jointly-owned U.S. Pat. Nos. 7,419,821 and 7,723,099 (referenced above) or U.S. Patent Application No. 61/288,189 (referenced above) provide a foundation for controlling the sample so that it is amended with reagents and allowed time to react before it passes through to the region of the conduit with the magnet. FIG. 7 illustrates the positioning of a rare earth permanent magnet R21 below an immunosensor chip within a cartridge housing in accordance with one embodiment of the present invention, and FIG. 8 illustrates a foldable cartridge of the type described in previously referenced U.S. Patent Application No. 61/288,189 (referenced above), where the magnet, e.g., rare earth permanent magnet (not shown), may be positioned underneath immunosensor chip 204 or one of the other adjacent chips.

Figure 9:
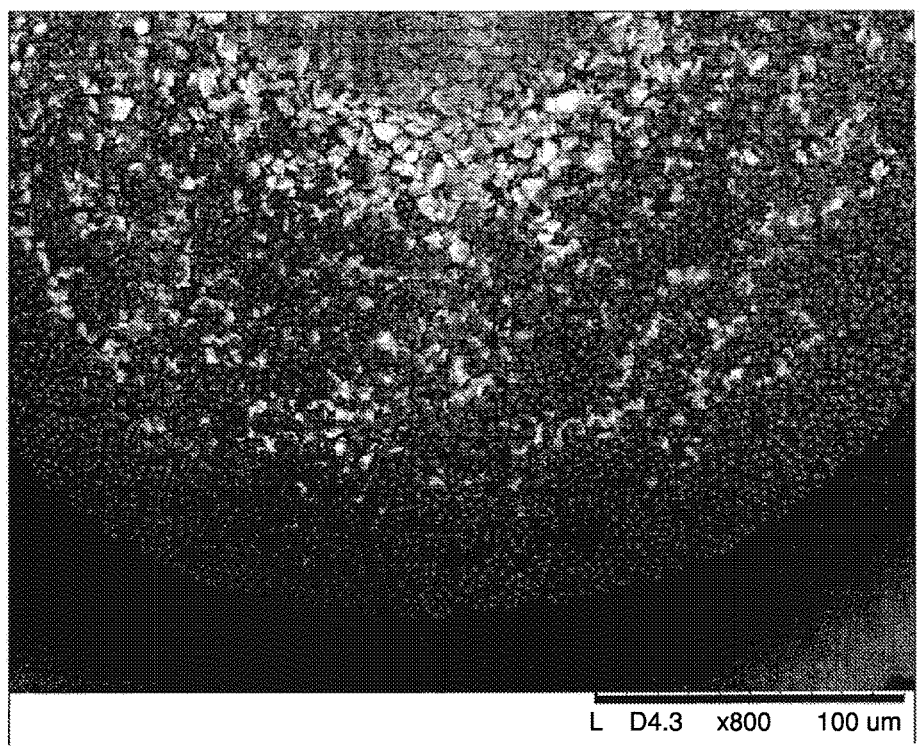
FIG. 9 is a micrograph of magnetically susceptible beads localized on a patterned magnetic layer of PVA and NdFeB particles.
Figure 10:
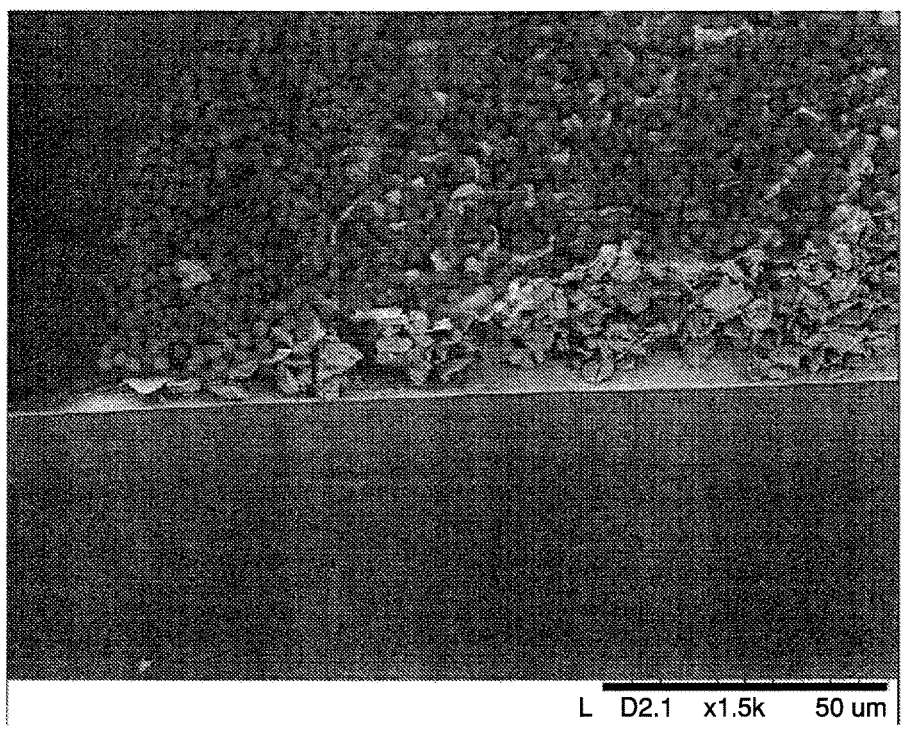
FIG. 10 is a micrograph of a fractured cross-section of the device of FIG. 9.

In some embodiments, an immunosensor is provided where the magnetic component is directly integrated into sensor manufacture, rather than being a separate component (e.g., bulk permanent high-field magnet) requiring assembly into the test device. For example, in one embodiment, a mixture of photoformable polyvinyl alcohol (PVA) mixed with ground $Nd_2Fe_{14}B$ powder was printed onto a wafer using a microdispensing apparatus of the type described in jointly-owned U.S. Pat. No. 5,554,339 (referenced above). The printed area was of a diameter of about 400 µm. After exposure to UV light and a wash step, the adhered layer was exposed to a solution of magnetically susceptible beads of about 3 µm diameter. The solution was then removed and the surface washed with buffer. FIG. 9 is a micrograph of a portion of the printed area where the relatively smaller ferromagnetic (dark) beads are accurately localized on the patterned magnetic layer. As shown, small areas of the relatively larger and irregular NdFeB (light) particles are observable below the beads. FIG. 10 is a micrograph of a fractured cross-section of the device in FIG. 9.

Figure 11A:
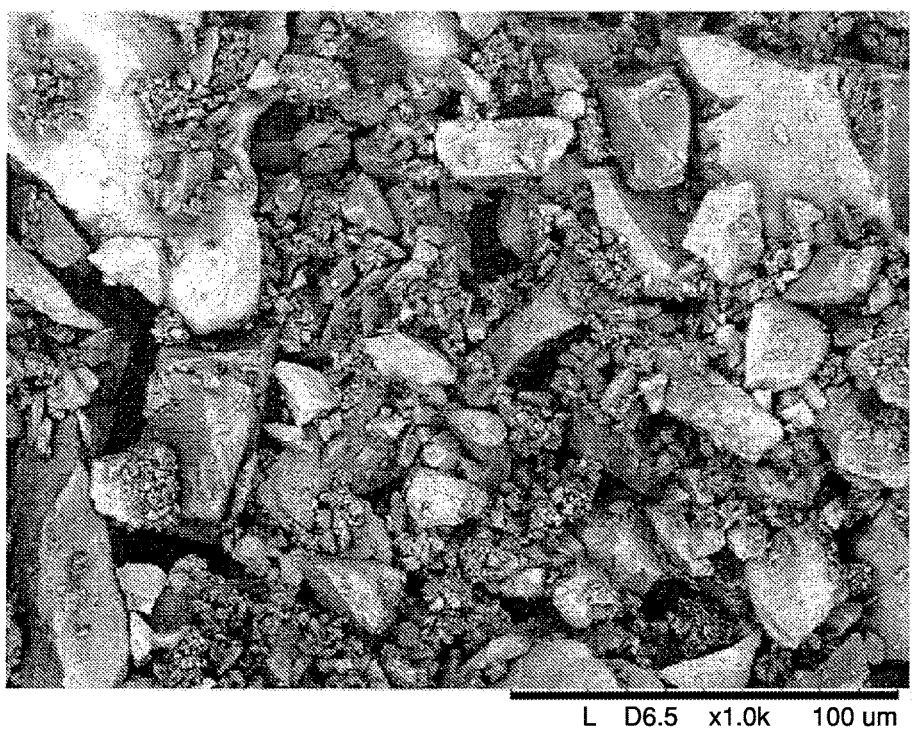
FIGS. 11A-C include micrographs of a patterned PVA film with various particle sizes of NdFeB (FIG. 11A); ground 6 μm MQP in polyimide (FIG. 11B); ground 6 μm MQP in polyimide (FIG. 11C)
Figure 11B:
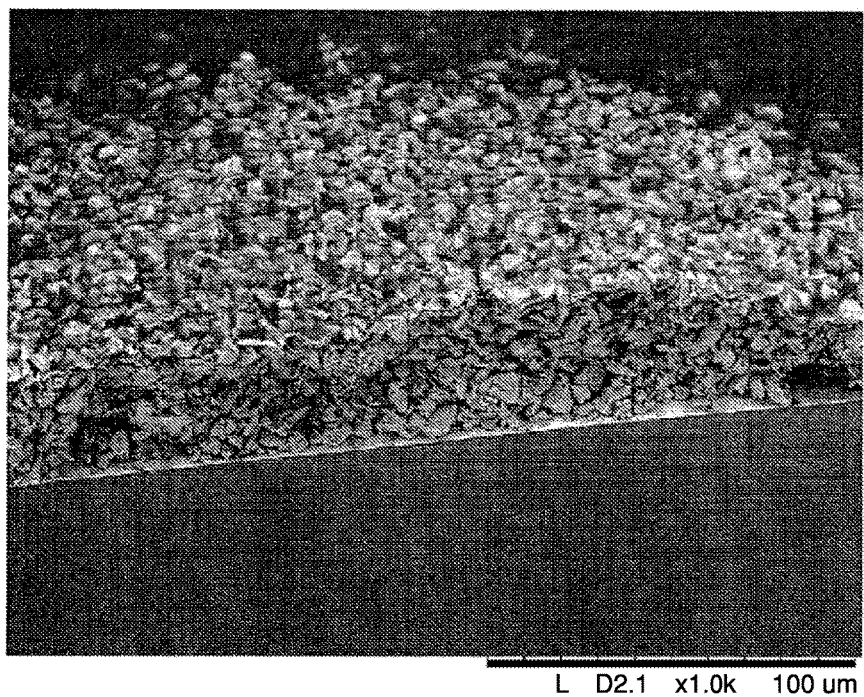
Figure 11C:
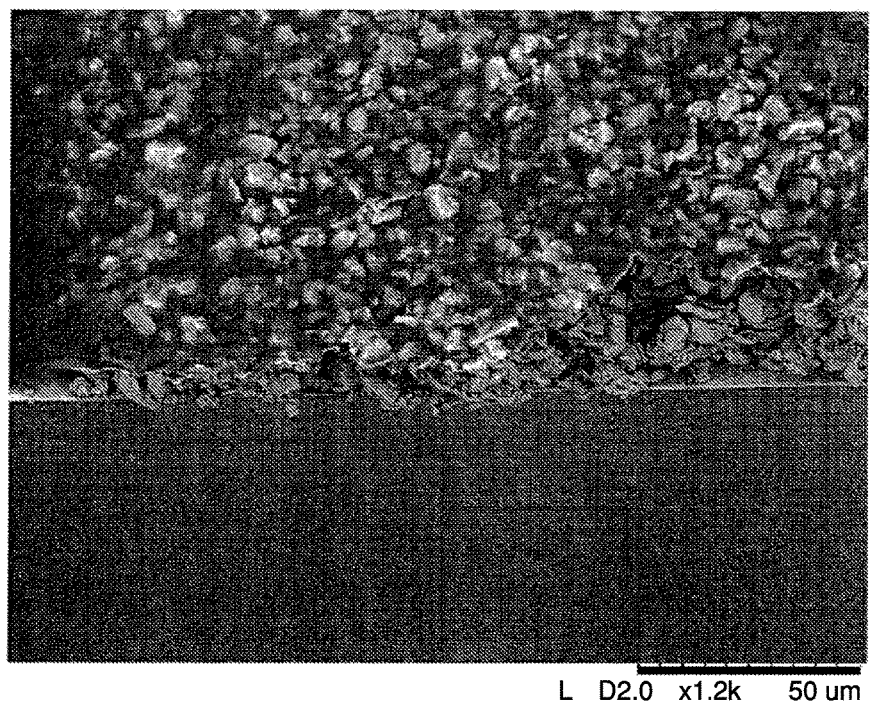

FIGS. 11A-C illustrate details of the patterned PVA and polyimide films with various particle sizes of NdFeB (FIG. 10A); ground 6 µm Magnaquench particles (MQP) in polyimide (FIG. 10B); and ground 6 µm. MQP in polyimide (FIG. 10C), before exposure to the magnetically susceptible beads. These types of layers were formed using Magnaquench particles (MQP), which is a NdFeB powder with an average particle size of about 6 µm in polyimide or Shipley Photo Resist (SPR).

It was found in accordance with certain embodiments of the invention that the about 3 µm to about 7 µm thick magnetic film of FIG. 9 was partially less effective in terms of capturing the beads than the about 30 µm to about 40 µm thick films of FIGS. 11A-C. While the "capture radius" of the embodiment of FIG. 9 was several tens of microns, the capture radius of the embodiment of FIGS. 11A-C was at least 200 µm. In preferred embodiments, the average capture radius of the sensors is less than about 500 µm, e.g., less than 300 µm or less than 250 µm. The shape and position of the magnet as well as its composition aid in the sensitivity and precision of assays using the techniques of the present invention.

Figure 12A:
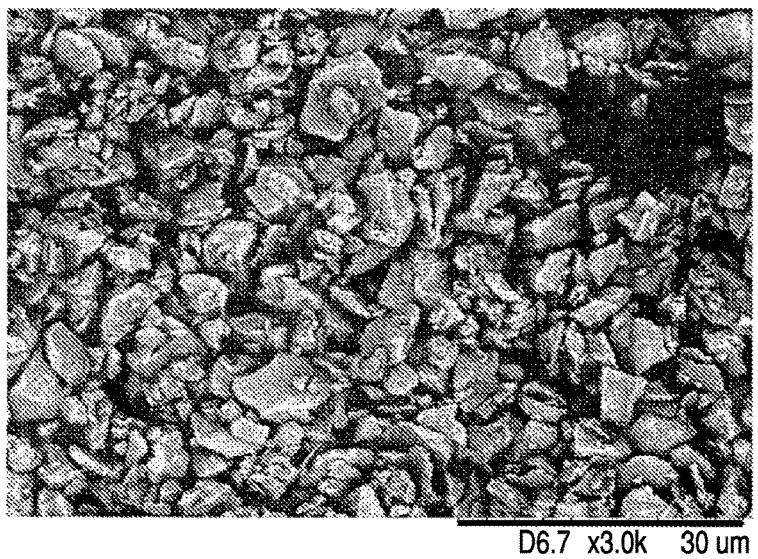
FIG. 12A is a micrograph of a 6 μm MQP NdFeB powder and FIG. 12B is a micrograph of the 6 μm MQP NdFeB powder comminuted using a ball mill.
Figure 12B:
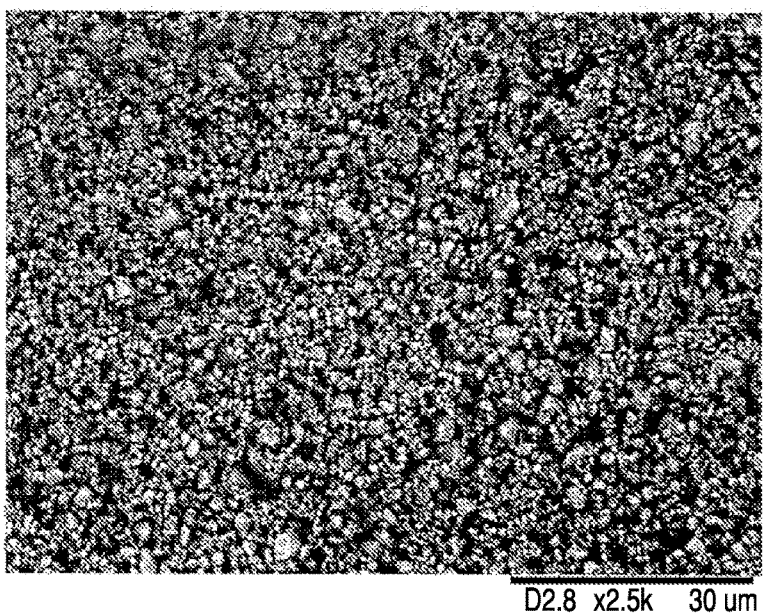
Figure 13:
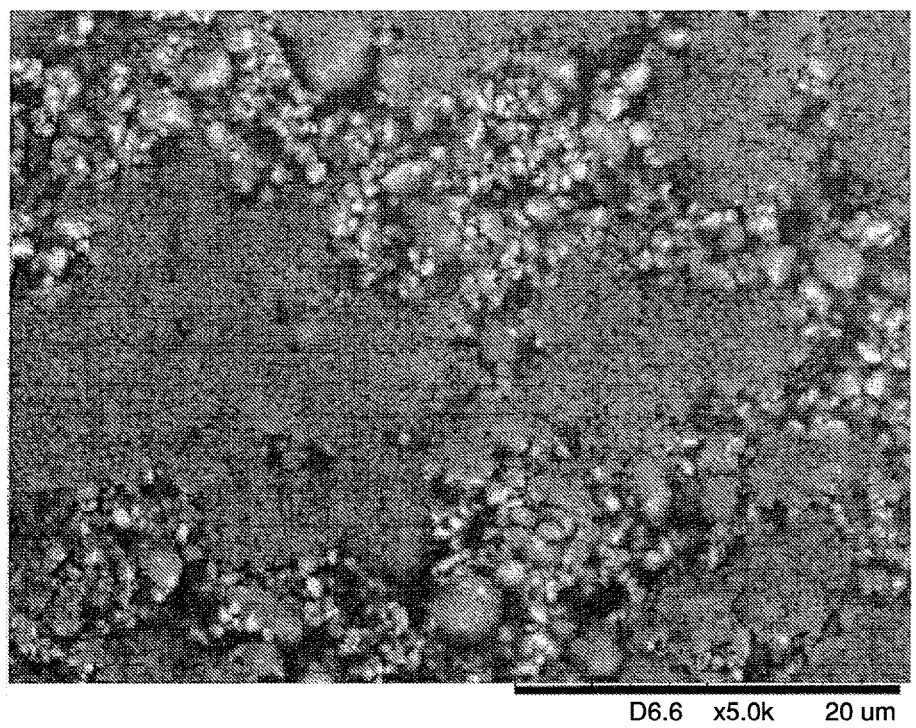
FIG. 13 is a micrograph of beads captured on NdFeB particle surfaces.

FIG. 12A is a micrograph of a MQP NdFeB powder with an average particle size of about 6 µm. FIG. 12B is a micrograph of the MQP NdFeB powder of FIG. 12A that has been comminuted via ball milling for about 3 days. In some embodiments, the comminuted NdFeB powder provides for a more homogeneous mobile magnetic composition, which may facilitate magnetic capture of the beads. FIG. 13 is a micrograph of beads captured on NdFeB particle surfaces. Those skilled in the art will recognize that caution should be taken during the grinding process to prevent combustion, e.g., adding 0.1 wt. % sulphur or cooling prior to opening the grinding container.

Figure 14A:
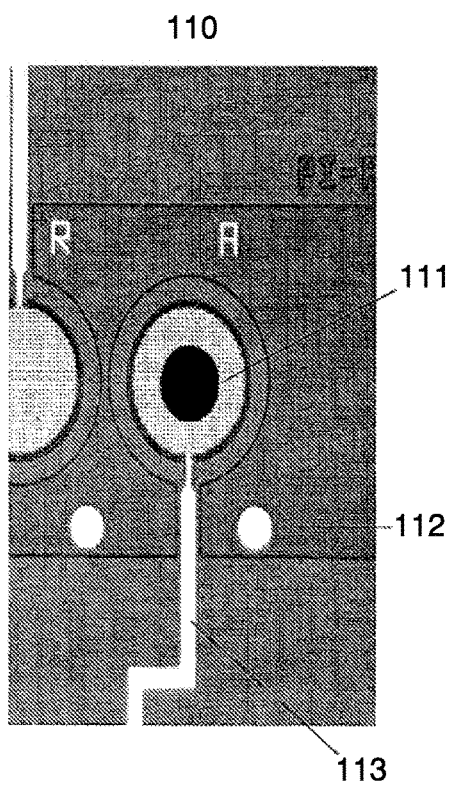
FIGS. 14A and 14B show exemplary base immunosensor electrode arrays partially covered with a printed NdFeB magnetic layer leaving a portion of the perimeter of the array exposed.
Figure 14B:
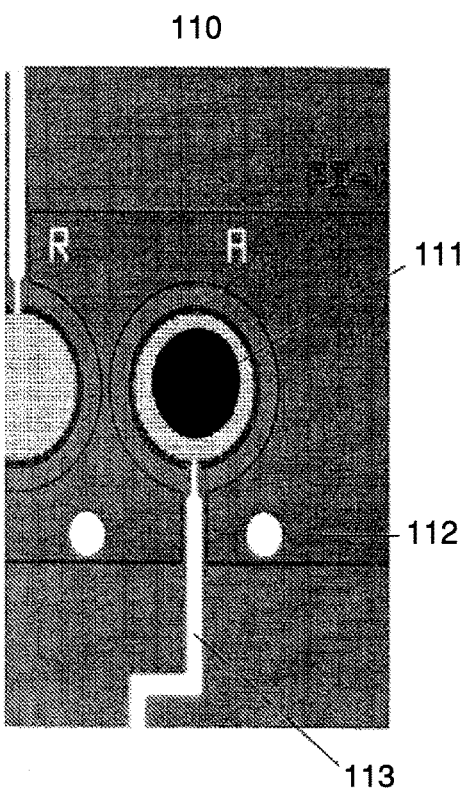
Figure 15A:
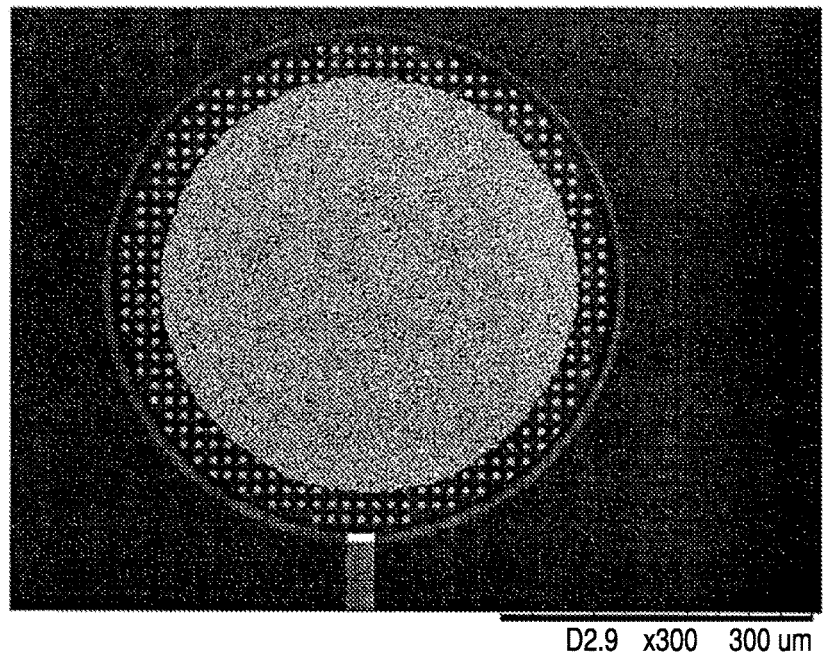
Figure 15A:
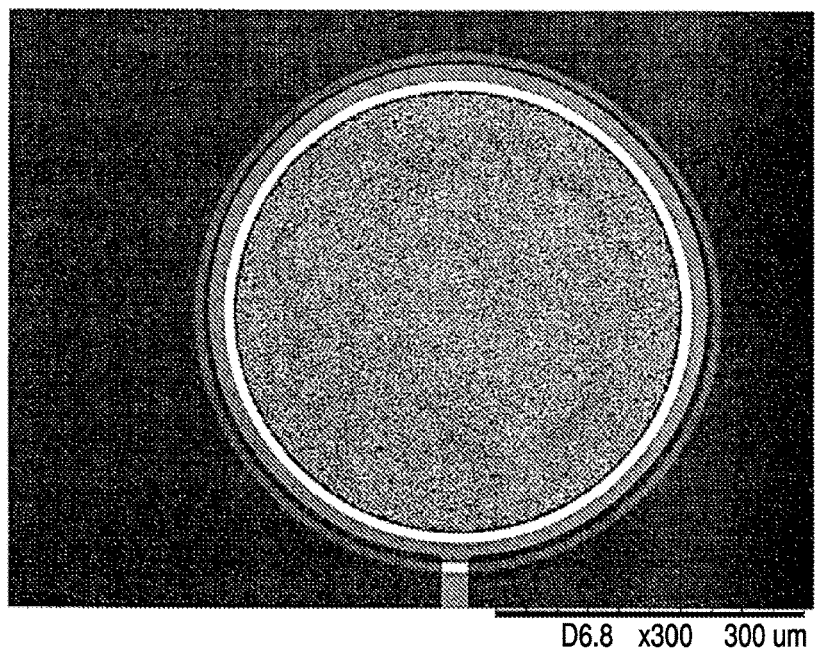
Figure 16:
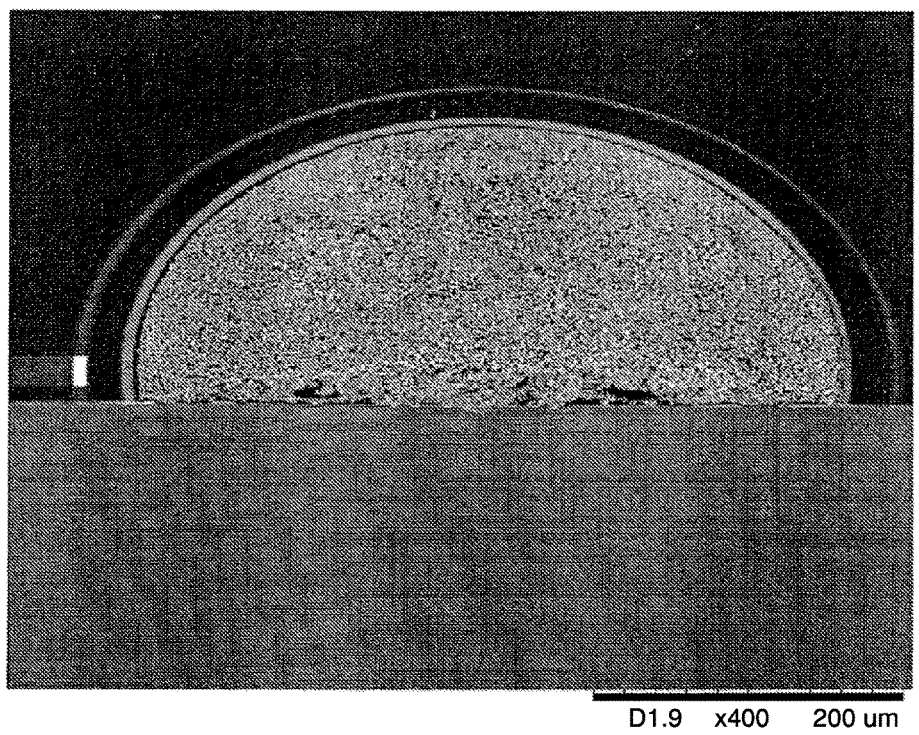
FIG. 16 is a sheared sensor illustrating the printed magnetic layer profile of FIGS. 15A and 15B.

FIGS. 14A and 14B show exemplary base immunosensor electrode arrays 110 partially covered with a printed polyimide and NdFeB particle matrix 111 leaving a portion of the perimeter of the array exposed. Also shown is the base silicon wafer 112 and a conductive line 113 for connecting the array to the instrument electronics. FIGS. 15A and 15B depict the over-printed magnetic layer in accordance with other embodiments of the present invention, where FIG. 15A is a standard microelectrode array and FIG. 15B is a single ring electrode having a width of about 20 µm. FIG. 16 is a sheared (i.e., fractured) sensor illustrating the printed magnetic layer profile of FIGS. 15A and 15B.

It is preferable that the high-field magnet, e.g., permanent or electromagnet, be within a few tens of microns of the amperometric sensor electrode surface in order to speed up the time constant (TC) of the sensor. In addition, it is preferable to size the magnet so that the attraction of the magnetically susceptible beads substantially dominates any of the potentially disruptive fluidic steps (e.g., washing), thereby "effectively permanently" trapping the reagent beads once captured on the immunosensor surface. While not being bound by theory, this is equivalent to a concept of an "event horizon" for the permanent magnet. "Effective permanent" capture relates to the attraction of a magnetic particle to the magnet, at the point at which the acceleration of the particle is greater than any of the potentially "disruptive" fluid motions (e.g., mixing oscillations and washing). Physical observation of this phenomenon with a microscope, therefore, can give a practical rough estimate of the "event horizon" for any given bead, sensor design and fluidic motion. Such information is useful in refining the overall test system design to achieve capture of substantially all or a reliable fraction (e.g., over 75 wt. %) of the beads from device to device. One intended use of the present invention is in making single-use disposable test cartridges in large volumes (i.e., greater than a million per year) and each device must perform reproducibly within a given batch, (i.e., have clinically acceptable precision and accuracy).

By way of example, in a preferred embodiment of a cTnI assay, a 10 µL segment of blood sample is oscillated over the immunosensor in a conduit of 0.5 mm height using a prototype design adapted from the i-STAT® immunoassay cartridge format. This process is performed with a 4 second cycle time (i.e., 4 Hertz) and equates to a maximum fluid velocity of about 10 cm per second. The magnetically susceptible beads are observed to move at about 10 µm per second in the direction of the magnetic field (microscope, jig and cartridge combination not shown). However, once the beads are within about 50 µm of the sensor surface, the beads are within the "event horizon" and become captured on the surface. The beads are no longer subject to the influence of the oscillation (i.e., resuspension of the particle is substantially negligible). Similarly, the trenched design of one embodiment of the present invention (with the intentional fabrication of a stagnant layer) may facilitate the retention of beads at the surface during this step.

Unlike assays where magnetically susceptible beads are always in contact with a liquid phase, in certain embodiments of the present invention, one or more intervening air segments are present between the sample and wash fluid in the conduit. (See, for example, U.S. Pat. No. 7,419,821 (referenced above)). Surprisingly and unexpectedly, it was found that the menisci formed by the air segments provide a greater shear force to the captured beads as they pass over the sensor than that generated by fluid oscillation where the beads are in constant contact with the liquid phase. It was also found that the slow passage of the menisci over the sensor surface was more disruptive than a relatively faster motion. The high-field magnets employed in the present invention (e.g., any material that provides a high magnetic field (e.g., greater than about 0.1 Tesla)) are preferable for optimizing movement of the magnetically susceptible beads in relation to the sensor.

Those skilled in the art will recognize that consistently and reliably retaining the captured beads on the sensor during the wash step is desirable in the delivery of accurate analytical results. While the addition of trenches on the sensor may be advantageous, selection of the appropriate field strength was also found to be a significant parameter. Experiments showed that greater than about 75% of the beads were retained on the surface during the wash step of the methods of the present invention. In one exemplary embodiment, the wash fluid comprises a 0.1 M diethanolamine buffer (pH 9.8), 1 mM $MgCl_2$, 1.0 M NaCl, 10 mM 4-aminophenylphosphate and 10 µM NaI.

With regard to the optimized test system design, the dimensions of the high-field magnet are important in that, generally, if the magnet is too small, either the time needed to capture the magnetically susceptible beads is too long or the stability (i.e., retained capture) during the washing step will degrade the assay performance. In addition, if the magnet is too deep below the sensor plane, or held too far away from the sensor surface, the force of attraction will be reduced and more diffuse and the magnetic reagents are poorly focused upon capture. Based on the present disclosure, those skilled in the art will understand how to optimize these various requirements for any given system and geometry (e.g., electrode area and position in a conduit).

Figure 17:
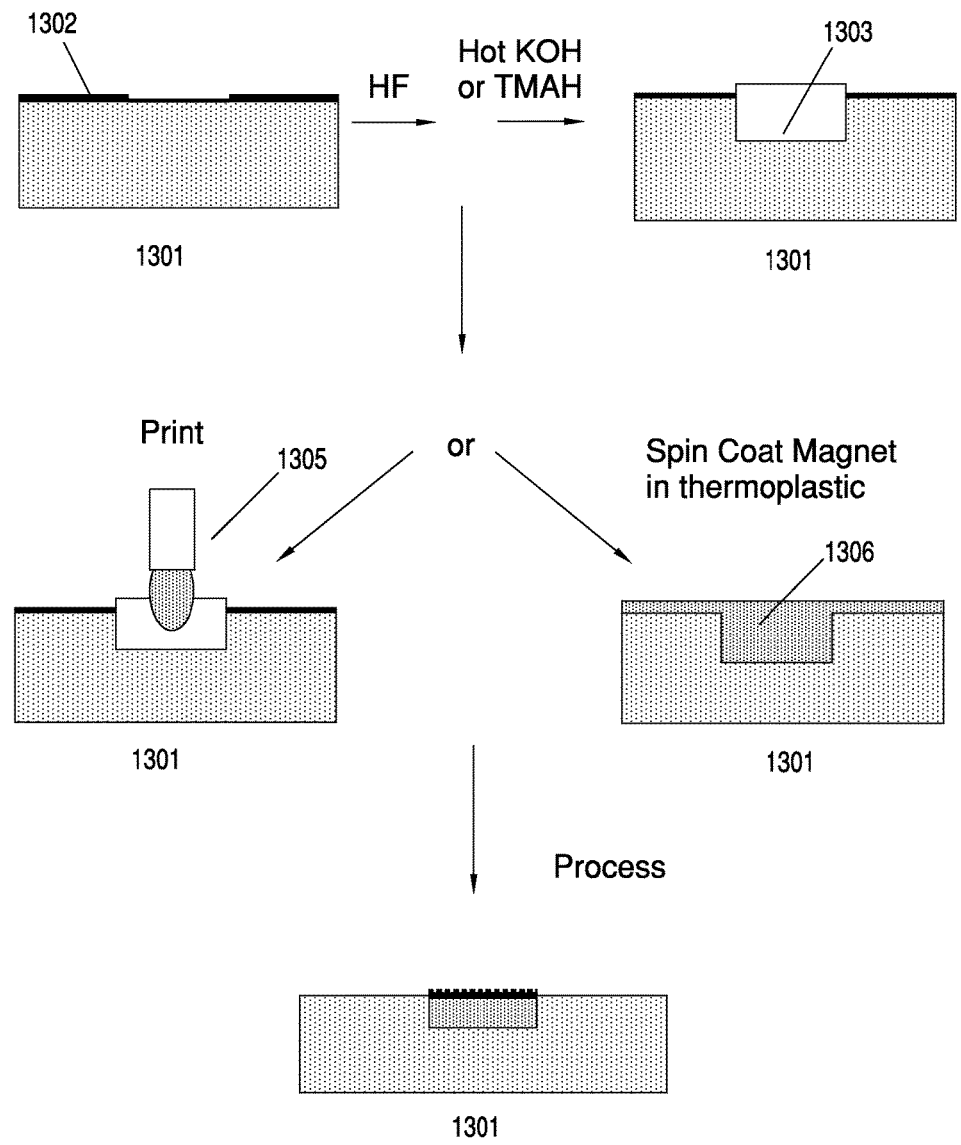
FIG. 17 illustrates the etched trench process in accordance with one embodiment of the present invention.

In some immunosensor embodiments, where the bulk permanent high-field magnet is positioned proximate to the sensing electrode or sensor (e.g., in the housing of the magnetic immunosensing device), the magnet diameter or width affects the time constant (TC) of the sensor and how effectively the sensor detects the signal-generating enzyme labels bound to the magnetic reagents on the magnet surface. Taking this into account as well as the relatively high topography designs shown in FIGS. 9 and 11A-C, vis-à-vis the common desire to perform wafer fabrication processing on substantially planar surfaces, the process illustrated in FIG. 17 was developed. FIG. 17 illustrates the etched trench process in accordance with one embodiment of the present invention, wherein a silicon wafer 1301 with a surface coating of photoresist 1302 is etched first with hydrofluoric acid (HF) and then with hot potassium hydroxide (KOH) or trimethyl ammonium hydroxide (TMAH) to leave a trench of controlled dimensions 1303 (e.g., a depth and width of from about 5 µm to about 200 µm). A slurry of magnetizable particles (e.g., NdFeB powder) in a thermoplastic matrix (e.g., polyimide) is then microdispensed 1305 or spin-coated 1306 into the trench thereby forming a substantially flat surface co-planar with the wafer 1301. The wafer 1301 may be further processed, as described in jointly-owned U.S. Pat. Nos. 7,419,821 and 7,723,099 (referenced above), to provide an immunosensor array over each etched trench on a wafer.

Figure 18:
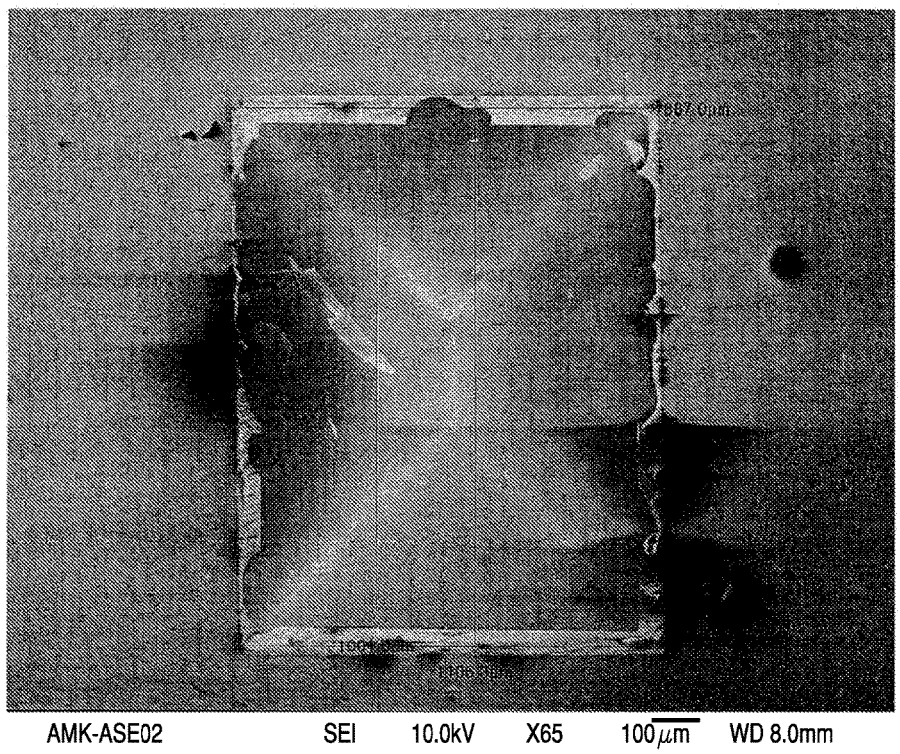
FIG. 18 is a top view of an exemplary underside trench design etched into a silicon wafer.
Figure 19:
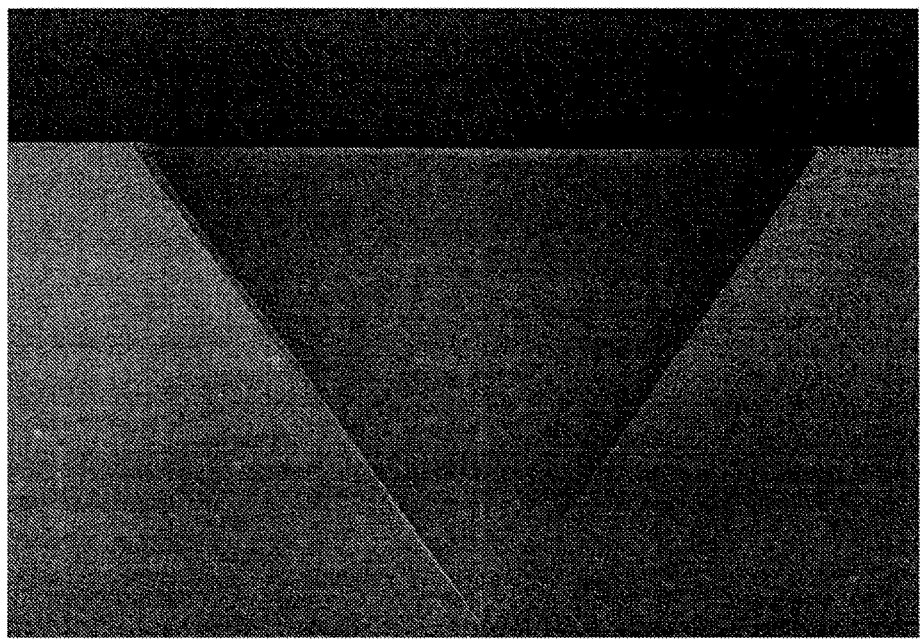
FIG. 19 is the cross-sectional profile of the underside trench.
Figure 20A:
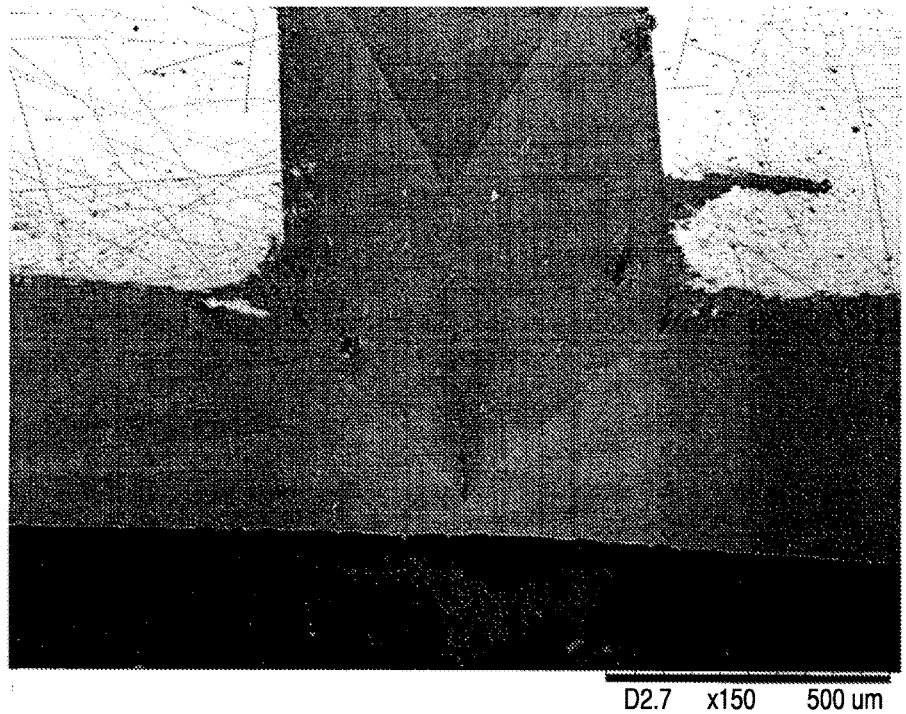
FIGS. 20A and 20B depict different views of the etched trench.
Figure 20B:
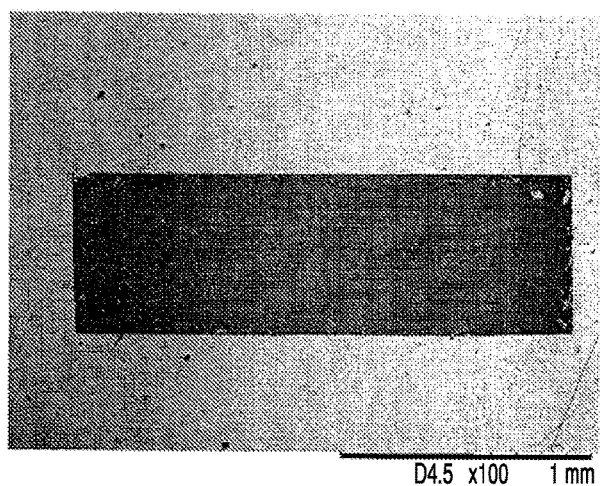
Figure 21:
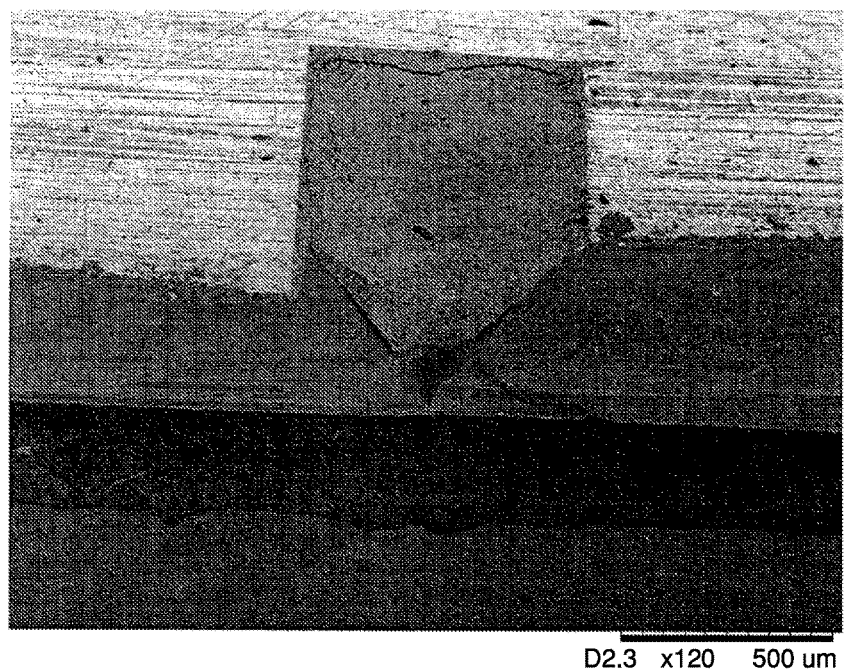
FIG. 21 shows the etched trench filled with NbFeB powder in a polyimide resin.
Figure 22A:
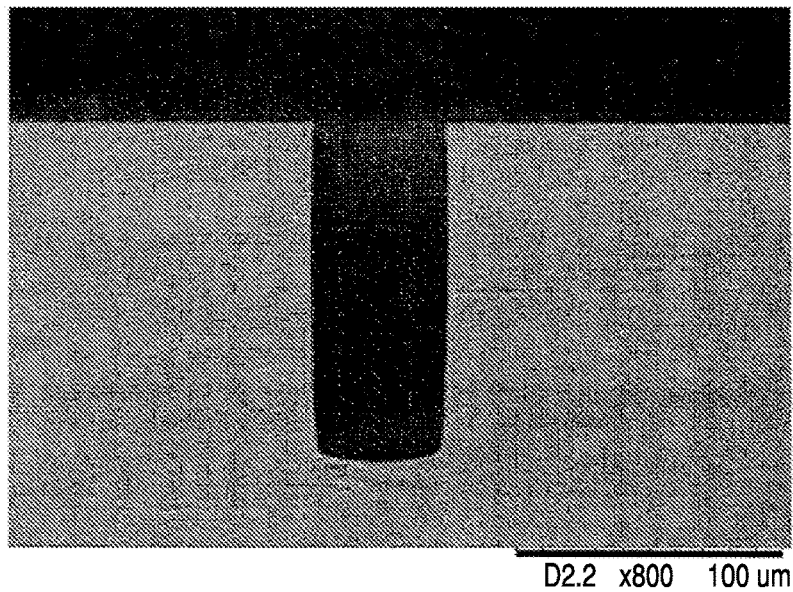
FIGS. 22A and 22B are micrographs of a rectangular trench produced on a silicon substrate via reactive ion etching.
Figure 22B:
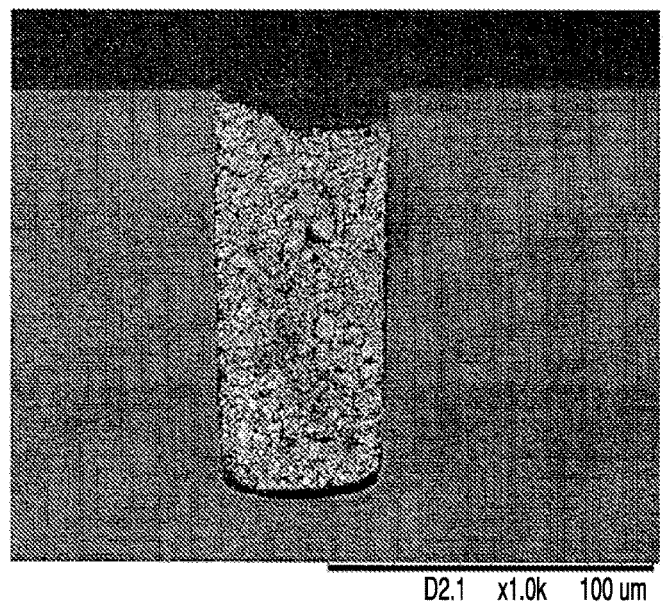

FIG. 18 is a top view of an exemplary underside trench design etched into a silicon wafer using a 800 µm×1000 µm mask. FIG. 19 is the after etch cross-sectional profile of the underside trench, having a depth of 50-90% into the silicon wafer. FIGS. 20A and 20B depict different views of the etched trench in accordance with one embodiment of the present invention and FIG. 21 depicts the trench filled with NbFeB powder in a polyimide resin. FIGS. 22A and 22B are micrographs of a rectangular trench produced on a silicon substrate via reactive ion etching by INO (Hamilton, Ontario). FIG. 22A shows a cross-section of the trench while FIG. 22B shows a different cross-section of the trench filled with NbFeB powder in a polyimide resin. The NbFeB powder was about 6 µm in diameter.

In another embodiment, the silicon wafer is polished on both sides and a trench is etched on one side and filled with magnetic particle material in a binder matrix. Sensor manufacturing processes in accordance with U.S. Pat. Nos. 7,419, 821 and 7,723,099 (referenced above) can then be performed on the other side of the wafer. This approach has the advantage of starting the electrode part of the sensor processes on a pristine flat surface. The binder matrix deposition step of the magnetic zone can optionally be performed as the last step in the overall process.

D. Hybrid Immunoassay

Figure 23:
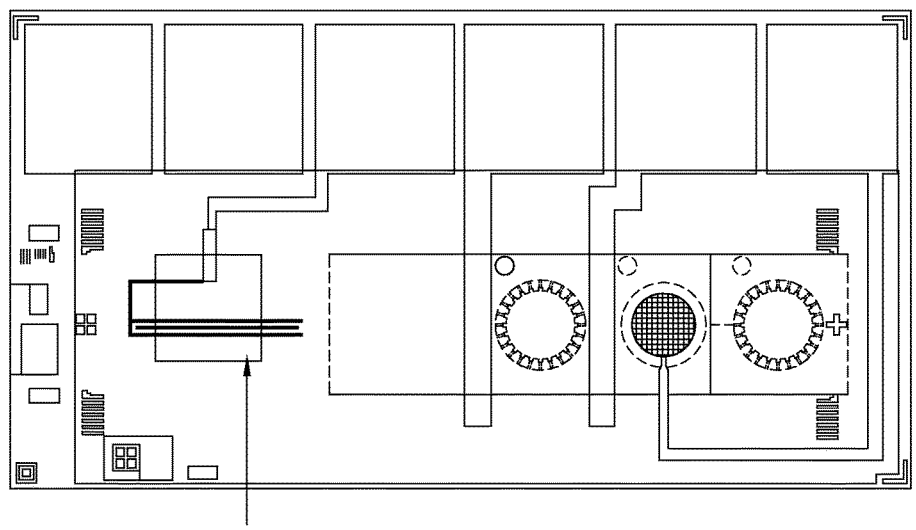
FIG. 23 depicts an exemplary combined sensor design for an expanded detection range where the magnetic zone is comprised a screen printed line of NdFeB powder in a polyimide matrix.
Figure 24:
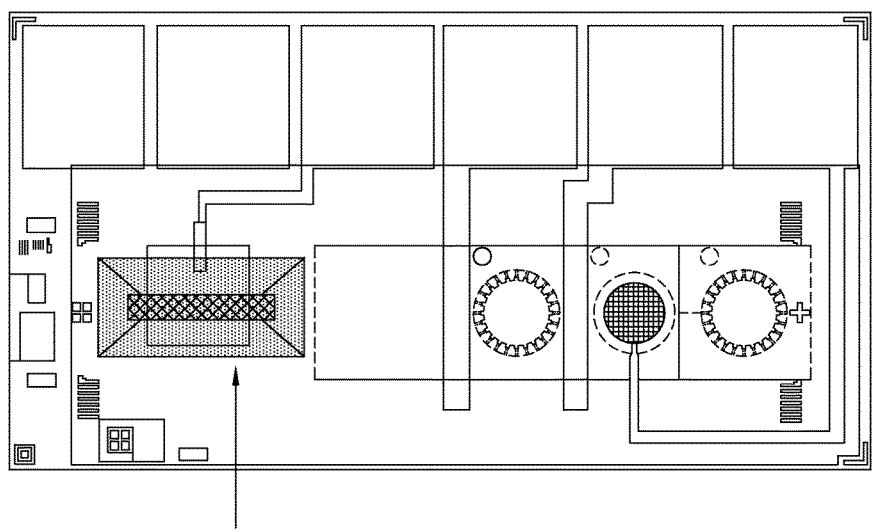
FIG. 24 depicts an exemplary combined sensor design for an expanded detection range where the magnetic zone is comprised of a bulk NdFeB magnet.
Figure 25:
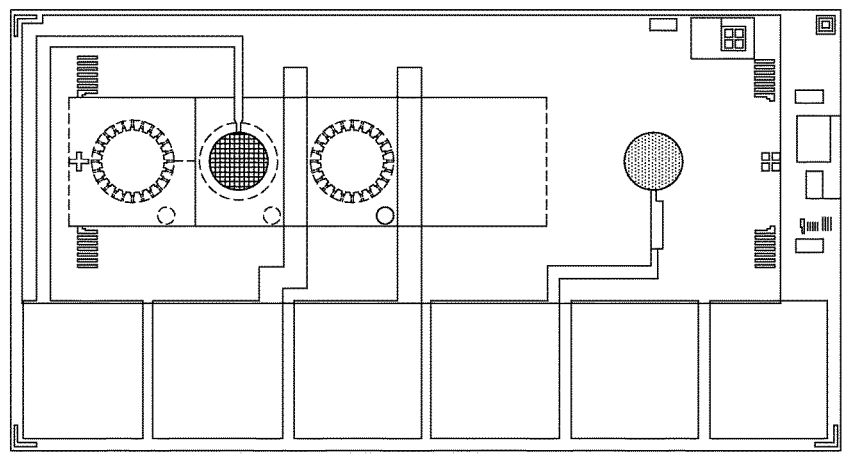
FIG. 25 depicts another combined sensor design in accordance with one embodiment of the present invention where the open circles on the chip are potential print locations for the reagents of the present invention.

In a hybrid test embodiment of the present invention, a current commercial cTnI assay (e.g., i-STAT cTnI cartridge) can be modified to include a separate but analytically integrated magnetic capture immunosensor. The prior art sensor covers the detection range of 0.20 ng/mL to 36.00 ng/mL, while certain embodiments of the magnetic capture immunosensor of the present invention cover a lower, but overlapping range of 0.002 ng/mL to 1.0 ng/mL. One such embodiment is shown in FIG. 23, where the magnetic zone is comprised a screen printed line of NdFeB powder in a polyimide matrix. Another embodiment is shown in FIG. 24, where the magnetic zone is comprised of a bulk NdFeB magnet having dimensions of 1.5 mm×100 µm×40 µm. Although the magnet appears to be positioned on the front side of the chip, it is truly positioned on the backside, and FIG. 24 is meant as a composite to show how the magnet and electrode are aligned. FIG. 25 depicts yet other exemplary combined sensor design where the open circles on the chip are potential print locations for the reagents of the present invention.

In one embodiment of the multiple amperometric magnetic immunosensor format, the background subtraction disclosed in jointly-owned U.S. Pat. No. 7,723,099 to Miller et al. is performed. U.S. Pat. No. 7,723,099 is hereby incorporated by reference in its entirety. This approach is optionally applied to both sensors, based on the inclusion of a reference immunosensor for the magnetic bar design. In an exemplary embodiment, the crossover from primary use of the magnetic sensor to the standard sensor enables a broad analytical range (e.g., from about 50 ng/mL to about 0.001 ng/mL for cTnI).

In a preferred embodiment, the use of the overlapping range sensors will include an instrument error detection software protocol, which enables an inconsistency between the cTnI sensor signals to be detected. For example, in the presence of sufficient cTnI in a test sample, both sensors should yield elevated signals, while in the absence of cTnI, both sensors should yield relatively low amperometric signals. Failure of these conditions being detected by the operating software would indicate that the analytical result is unreliable. Consequently, the instrument would suppresses reporting a result and instead indicate to the user that the test should be re-run with a new cartridge.

In yet another embodiment, the stabilization of the reagents and mode of printing enables a quick curing matrix. Print cocktails for the enzyme conjugate include, but are not limited to the enzyme-labeled antibody to the analyte in a protein stabilizing matrix of less than 30% solids and more preferably 10% or lower solids. The printed magnetic materials of the present invention cure rapidly (i.e., in less than about 7 days). This relatively quick curing time has the advantage of simplifying the manufacturing process, where a short delay between chip manufacture and assembly into a cartridge is desirable.

IV. Oscillating Magnetic Immunoassays

While the disclosure above generally is based on the concept of a static magnetic field localized in the region of the immunosensor, an alternative methodology is also envisaged where an oscillating magnetic field is used adjacent to the immunosensor.

One oscillating magnetic field embodiment makes critical use of labeled magnetically susceptible beads containing both a label antibody, and an enzyme or fluorescent marker or any other detectable label, termed herein as a "signaling moiety." The label may be detected by any means known in the art including simple microscopy or a reflectance measurement for the beads attached to the capture site using an immunosensing device. In addition, the label can be measured optically through a simple optical density measurement on the capture regions or electrochemically, e.g., through an enzymatic reaction. Additional detection techniques include optical resonators, nuclear magnetic resonance (NMR), piezoelectric, pyroelectric, fluorescence, chemiluminescence and surface acoustic wave, among others.

Another embodiment of the invention is to a method of performing a sandwich immunoassay for an analyte in a sample with an immunosensor on a substantially planar surface using a means for applying an oscillating magnetic field (e.g., an electromagnet and/or a moving fixed magnet with respect to the surface of the immunosensor). The first step comprises mixing the magnetically susceptible beads with a sample containing or suspected of containing an analyte, wherein the beads are coated with an antibody to the analyte and a signal generating moiety. The second step requires oscillating the beads across the surface of the immunosensor coated with a second antibody to the analyte, using one of the magnetic means mentioned above. An antibody sandwich is formed thereby immobilizing the beads on the immunosensor. The sample is then washed from the immunosensor, and the signaling moiety on the immunosensor is detected.

Various embodiments of the invention are directed to use of the movement of the magnetically susceptible beads along a surface to accelerate the signal generation of an immunoassay. In one embodiment, the beads are initially located in a region between two spaced magnetic zones and can move freely between the two. Oscillation of the magnetic field may start slowly and increase in frequency and the magnetically susceptible beads are forced to move back and forth across a surface as the field changes. Through this motion, the beads can be captured in the intervening space on a capture area of the immunosensor having capture antibodies for a particular target analyte. In a preferred embodiment, the beads are labeled with analyte specific antibody or antibodies.

Figure 26:
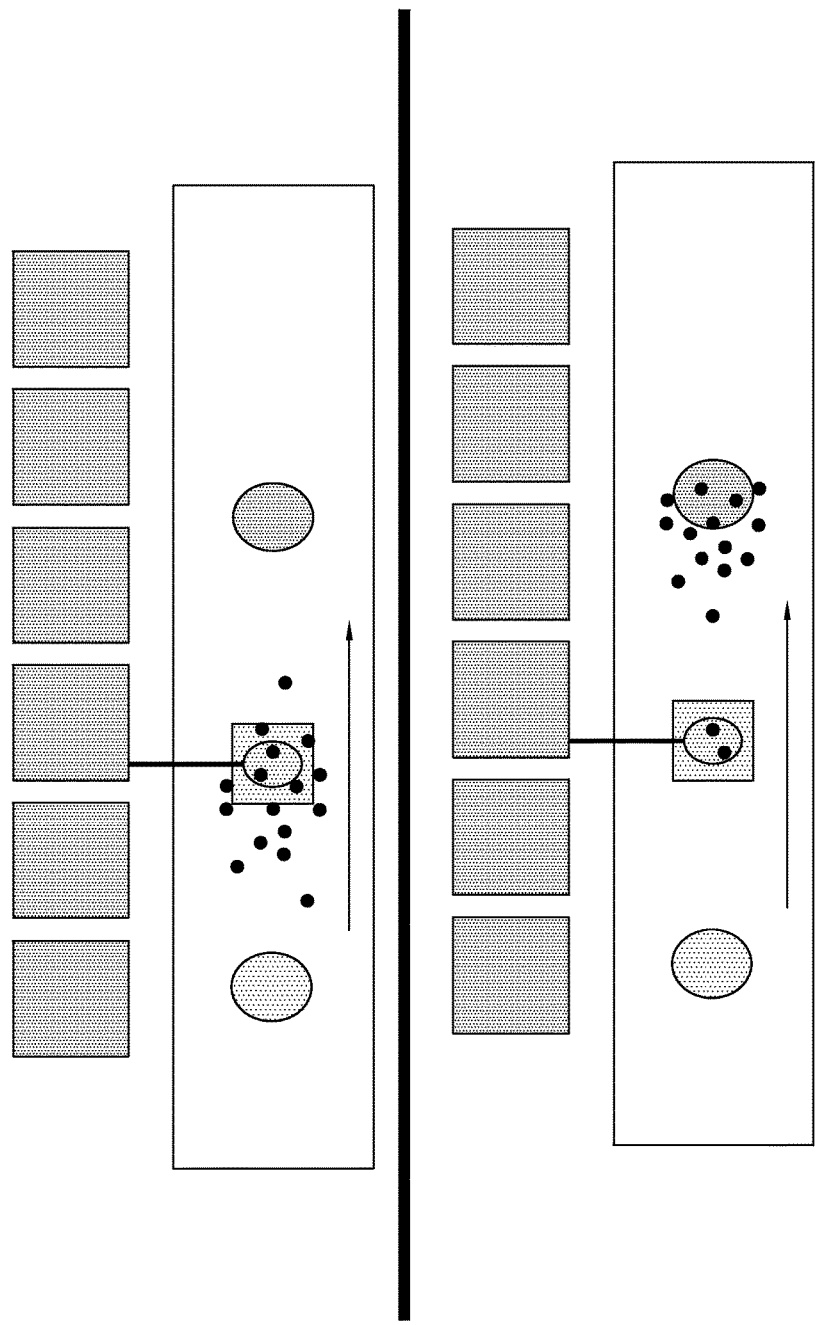
FIG. 26 is a schematic of an oscillating bead immunoassay (OBIA) with a central immunosensor flanked by two adjacent magnetic zones with the small bead moving in-between in accordance with one embodiment of the present invention.
Figure 27:
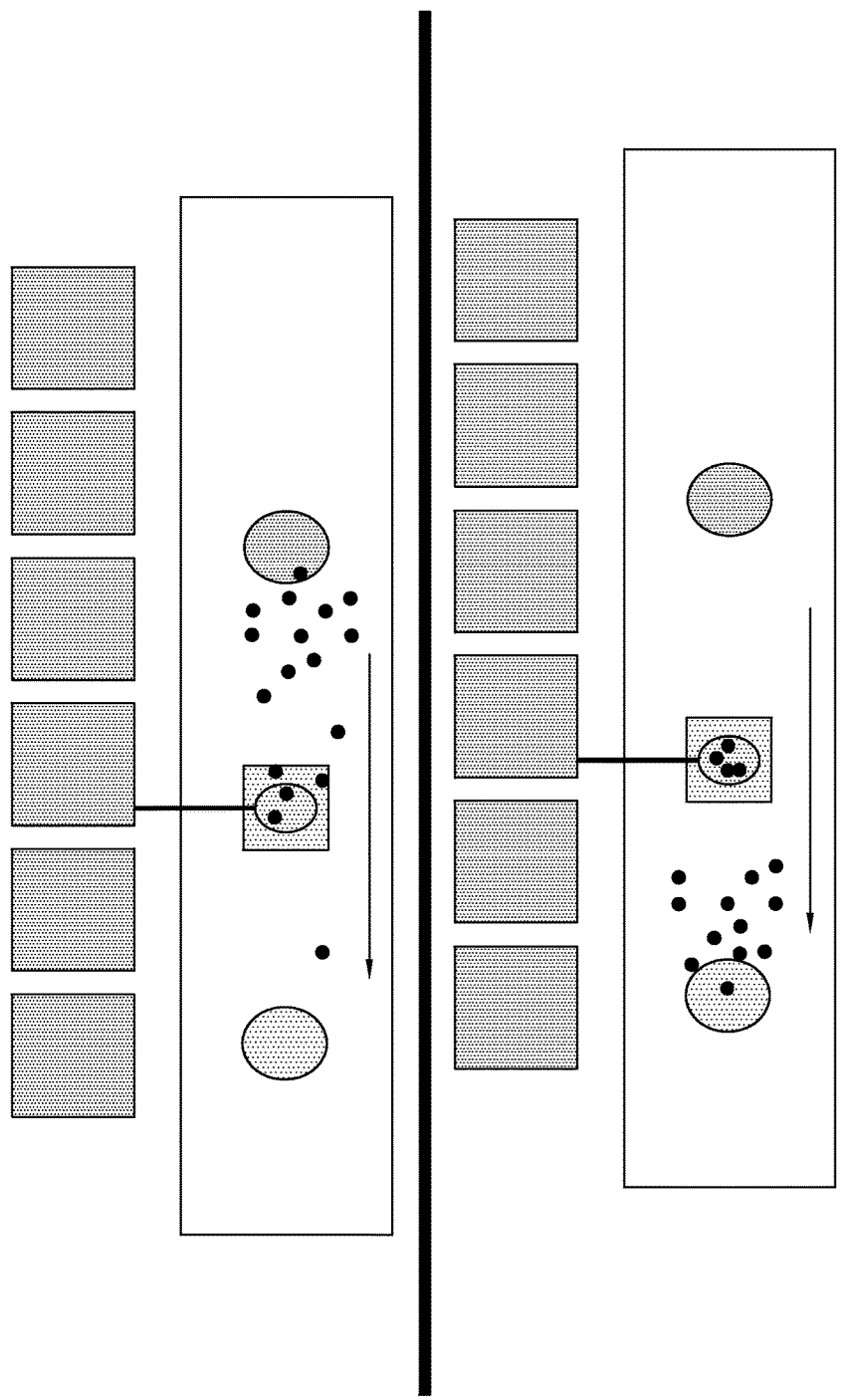
FIG. 27 is a schematic illustrating the degree of bead capture with time.
Figure 28:
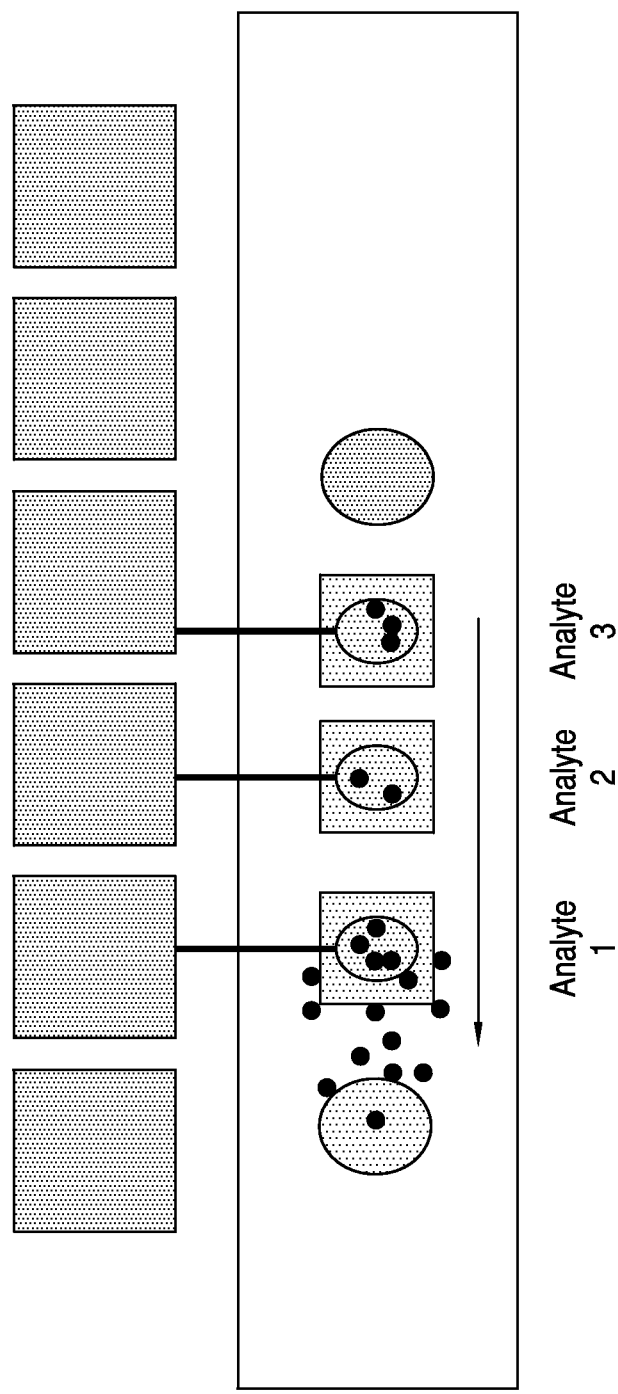
FIG. 28 shows a multiplexed OBIA where several different types of analyte-capturing beads are present, but where they are effectively separated onto their individual capture sites.

FIG. 26 is a schematic of an oscillating bead immunoassay (OBIA) with a central immunosensor flanked by two adjacent magnetic zones with the magnetically susceptible beads moving there between, and FIG. 27 shows the enhanced degree of bead capture with time in accordance with one embodiment of the present invention. These immunoassay embodiments are amenable to multiplexing, i.e., testing for more than one type of analyte, because the capture event is localized by the capture immunosensor's specificity to a particular analyte. FIG. 28 illustrates a multiplexed OBIA where several different types of analyte-capturing beads are present, but where they are effectively separated onto their individual capture sites (e.g., separate immuno sensors).

As shown in FIG. 28, the format of the OBIA can be multiplexed with the specific capture regions for the different analytes to be measured being arranged sequentially between the two magnetic concentration areas. A reference sensor (not shown) is also readily applied in this format by having a non-specific antibody layer with the series of specific analyte capture sites. In this embodiment, the magnetically susceptible beads are prepared containing label antibodies thereon and are mixed together in controlled ratios, depending on the analytical considerations of the particular assays within the multiplexed immunoassay cartridge. All of the labeled magnetically susceptible beads will then move between the two magnet contact zones across each of the specific capture regions. The different analyte-specific magnetically susceptible beads may have the same label type or, more preferably, will have different types of labels. Optionally, the different analyte-specific magnetically susceptible beads can be mixed into the same sample and allowed to react prior to their attraction to the sensor surface via the positioning of the magnets.

Those skilled in the immunosensing art will recognize that this assay format relies on the capture of the beads as they traverse over the surface in the presence of the magnet fields generated on either side of the capture areas. As such, the sensor signal-to-noise ratio is dependent on making non-specific binding minimal on the surface except where the specific capture antibodies are deposited. An important feature of one embodiment of the invention is, therefore, to employ pairs of immunosensors (e.g., electrodes) with indifferent antibodies where the second one acts as a reference sensor. Here, the second sensor signal is subtracted from the first one of the pair. This general concept is disclosed in jointly-owned U.S. Pat. No. 7,723,099 (referenced above).

In another variant of the present embodiment, the oscillation of the beads is kept to one side of the capture region for a period of time in order to allow analyte capture on the immunosensor surface. A further refinement includes a reference sensor to determine the portion of the non-specific signal generated during the analyte capture part of the assay. The magnetic field is preferably actuated via a coil around two ends of a tube or conduit, similar to, for example, the formation of NMR shim fields. This allows control of the force the magnetically susceptible beads experience in contacting the surface of the sensor and minimizes nonspecific binding. Here, the coils have several axes to allow x/y and z motion in the conduit. Fixed magnets on a rotating or oscillating platform may be used in alternative embodiments.

EXAMPLES

The present invention will be better understood with reference to the specific embodiments set forth in the following non-limiting examples.

Example 1

Immunoassay for Determination of Troponin I (TnI)

Figure 29:
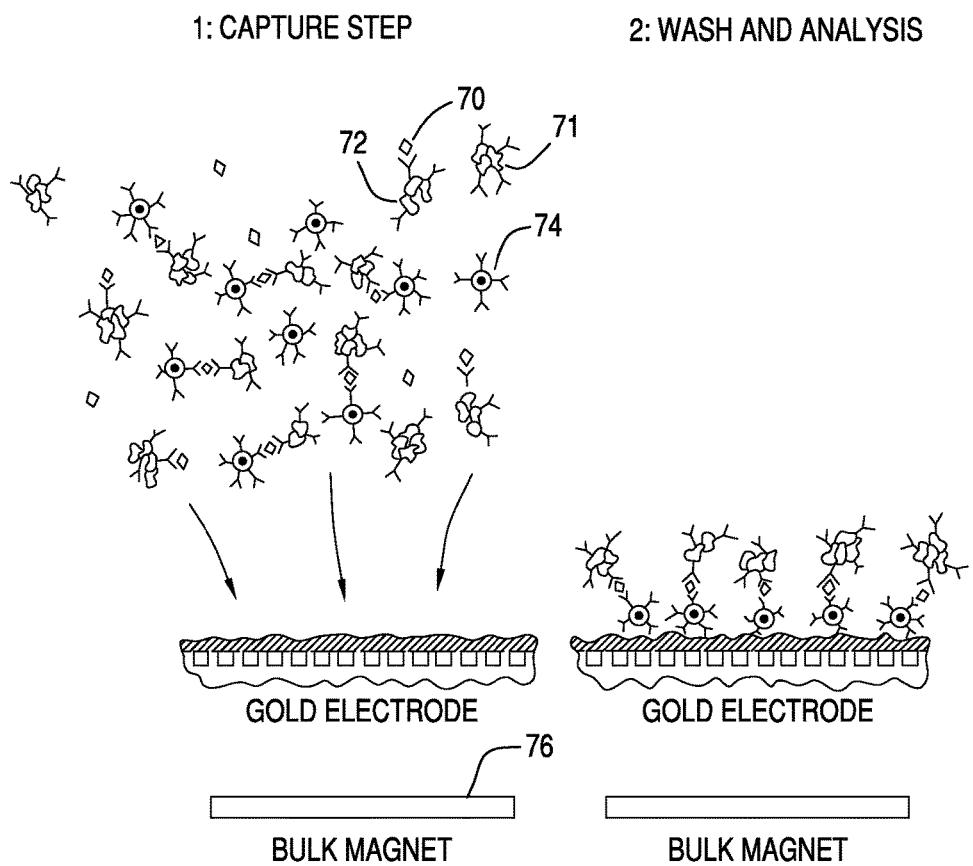
FIG. 29 illustrates the comparative principle of an amperometric immunoassay for determination of troponin I (TnI), a marker of cardiac injury.
Figures 30, 31:
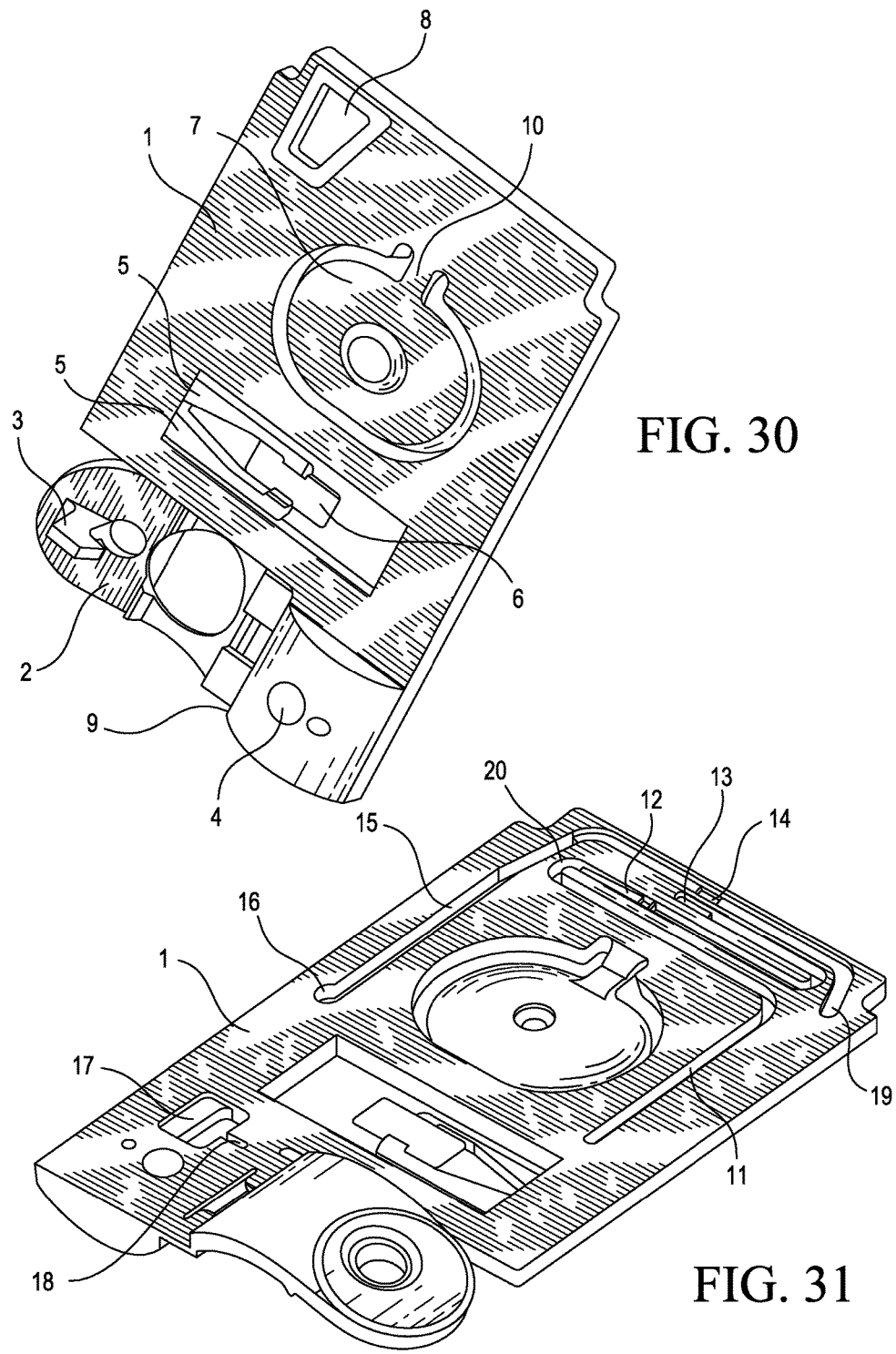
FIG. 30 is an isometric top view of an immunosensor cartridge cover of one embodiment of the invention.
FIG. 31 is an isometric bottom view of an immunosensor cartridge cover of one embodiment of the invention.
Figure 32:
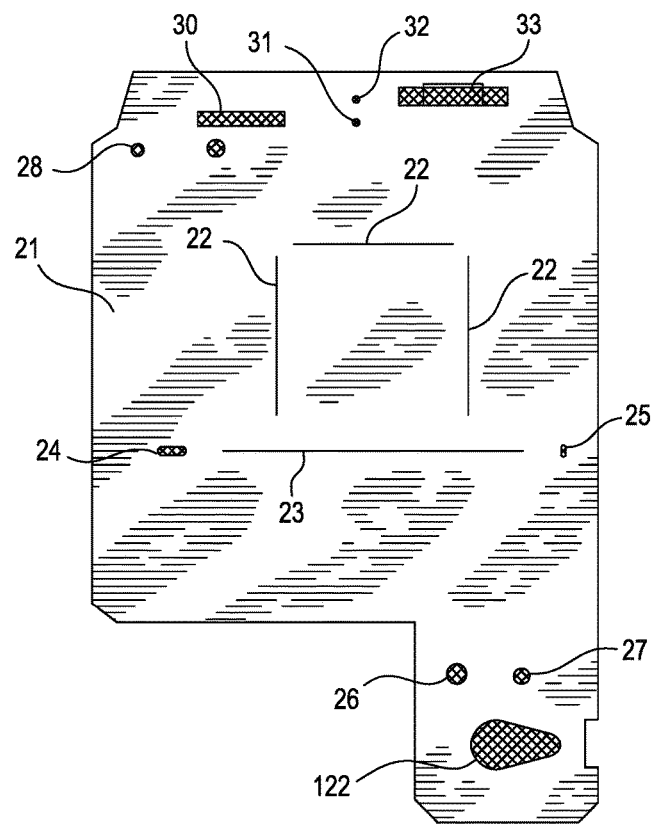
FIG. 32 is a top view of the layout of a tape gasket for an immunosensor cartridge of one embodiment of the invention.
Figure 33:
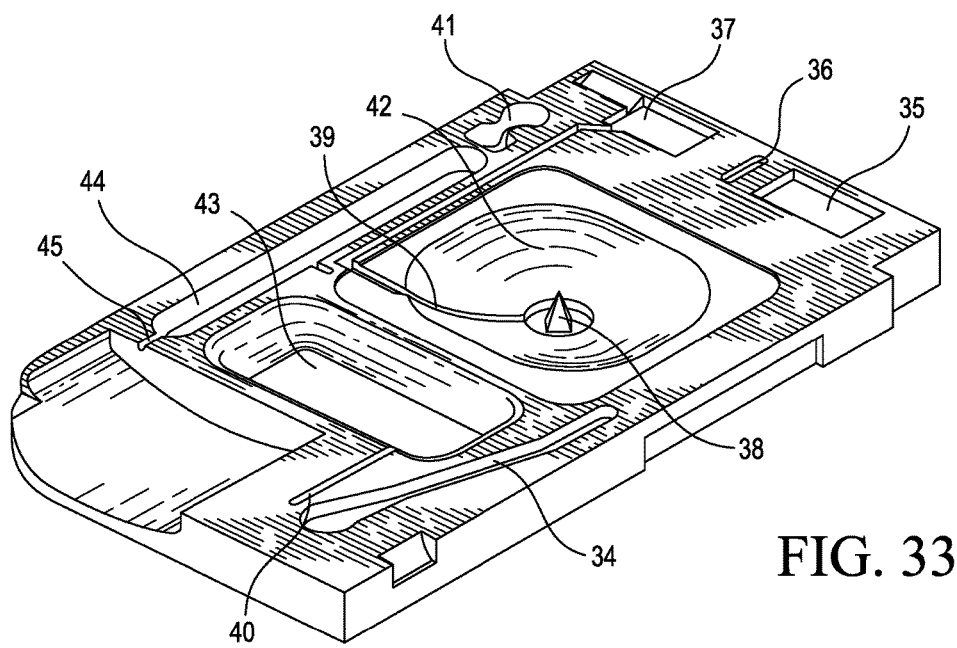
FIG. 33 is an isometric top view of an immunosensor cartridge base of one embodiment of the invention.

FIG. 29 illustrates a comparative amperometric immunoassay for the determination of troponin I (TnI) 70, a marker of cardiac injury. In one embodiment, a blood sample, for example, is introduced into the sample holding chamber of the immunosensing device of the present invention, and is amended by a conjugate molecule 71 comprising alkaline phosphatase enzyme (AP) covalently attached to a polyclonal anti-troponin I antibody (cTnI). This conjugate specifically binds to the TnI 70 in the blood sample, producing a complex made up of TnI bound to the AP-aTnI conjugate 72. The blood sample is further amended with polymer beads with a ferrite core 74 coated with a TnI antibody. The mixture is oscillated in a conduit connected to the holding chamber that generates sandwich formation on the bead.

Positioned in the conduit is the sensor chip (or chips), which includes a conductivity sensor used to monitor where the sample is with respect to the sensor chip. The position of the sample segment within the conduit can be actively controlled using the edge of the fluid as a marker. As the sample/air interface crosses the conductivity sensor, a precise signal is generated that can be used as a fluid position marker from which controlled fluid excursions can be executed. The fluid segment is preferentially oscillated edge-to-edge over the sensor. The immunosensor chip is positioned downstream of the mean oscillation position in the conduit. A bulk magnet 76 is positioned under the sensor chip and draws the magnetically susceptible beads to the immunosensor surface.

In the present example, the sensor comprises an amperometric electrode used to detect the enzymatically produced 4-aminophenol from the reaction of 4-aminophenylphosphate with the enzyme label alkaline phosphatase. The electrode is preferably produced from a gold surface coated with a photodefined layer of polyimide. Regularly spaced openings in the insulating polyimide layer define a grid of small gold electrodes at which the 4-aminophenol is oxidized in a 2 electron per molecule reaction.

Substrates, such as p-aminophenol species, can be selected such that the half-wave potential ($E_{1/2}$) of the substrate and product differ substantially. Preferably, the $E_{1/2}$ of the substrate is substantially higher (i.e., more positive) than that of the product. When this condition is met, the product can be selectively electrochemically measured in the presence of the substrate.

The detection of alkaline phosphatase activity in this example relies on a measurement of the 4-aminophenol oxidation current. This is achieved at a potential of about +60 mV versus the Ag/AgCl reference electrode on the chip. The specific form of detection used depends on the sensor configuration. The concentration of the 4-aminophenylphosphate is selected to be in excess, e.g., 10 times the Km value. The analysis solution is 0.1 M in diethanolamine and 1.0 M NaCl, buffered to a pH of 9.8. Additionally, the analysis solution contains 0.5 mM $MgCl$, which is a cofactor for the enzyme. A carbonate buffer may alternatively be utilized.

In various embodiments, the antibodies are selected to bind one or more of protein, e.g., human chorionic gonadotrophin, troponin I, troponin T, troponin C, a troponin complex, creatine kinase, creatine kinase subunit M, creatine kinase subunit B, myoglobin, myosin light chain, or modified fragments thereof. Such modified fragments are generated by oxidation, reduction, deletion, addition or modification of at least one amino acid, including chemical modification with a natural moiety or with a synthetic moiety. Preferably, these biomolecules bind to the analyte specifically and have an affinity constant for binding of about $10^7$ to $10^{15}$ $M^{-1}$.

The immunosensor was prepared as follows. A silicon wafer was thermally oxidized to form an insulating oxide layer with a thickness of about 1 µm. A titanium/tungsten layer was sputtered onto the oxide layer to a preferable thickness of about 100 Å to about 1000 Å, followed by a layer of gold that is most preferably about 800 Å thick. A photoresist was then spin coated onto the wafer and was dried and baked. The surface was then exposed using a contact mask, and the latent image was developed. Next, the wafer was exposed to a gold-etchant. The patterned gold layer was coated with a photodefinable polyimide, suitably baked, exposed using a contact mask, developed, cleaned in an $O_2$ plasma, and preferably imidized at 350° C. for 5 hours. An optional metallization of the back side of the wafer may be performed to act as a resistive heating element, such as for example in embodiments where the immunosensor is to be used in a thermostatted format.

Example 2

Magnetic Immunosensing Device and Method of Use

The present example describes a method of using a magnetic immunosensing device in accordance with one embodiment of the invention. As shown in FIGS. 30-33, an unmetered fluid sample was introduced into sample chamber 34 of a cartridge, through a sample entry port 4. Capillary stop 25 prevents passage of the sample into conduit 11 at this stage, and conduit 34 is filled with the sample. Lid 2 is closed to prevent leakage of the sample from out of the cartridge. The cartridge is then inserted into a reading apparatus, such as that disclosed in U.S. Pat. No. 5,821,399 to Zelin (referenced above), which is hereby incorporated by reference. Insertion of the cartridge into a reading apparatus activates the mechanism which punctures a fluid-containing package located at 42 when the package is pressed against spike 38. Fluid is thereby expelled into the second conduit, arriving in sequence at 39, 20, 12 and 11. The constriction at 12 prevents further movement of fluid because residual hydrostatic pressure is dissipated by the flow of fluid via second conduit portion 11 into the waste chamber 44. In a second step, operation of a pump means applies pressure to air-bladder 43, forcing air through conduit 40, through cutaways 17 and 18, and into conduit 34 at a predetermined location 27. Capillary stop 25 and location 27 delimit a metered portion of the original sample. While the sample is within sample chamber 34, it is optionally amended with a compound or compounds present initially as a dry coating on the inner surface of the chamber (e.g., antibody-coated magnetically susceptible beads and enzyme-labeled antibody conjugate). The metered portion of the sample is then expelled through the capillary stop by air pressure produced within air-bladder 43. The sample optionally is oscillated in order to promote efficient sandwich formation on the magnetically susceptible beads. Preferably, an oscillation frequency of between about 0.2 Hz and about 5 Hz is used, most preferably about 0.7 Hz.

In the next step, the sample is moved forwards along the conduit such that the magnetically susceptible beads can become trapped onto the surface of the magnetic electrode. Subsequently, the sample is ejected from the conduit by further pressure applied to air-bladder 43, and the sample passes to waste chamber 44. A wash step next removes non-specifically bound enzyme-conjugate from the immunosensor area of the conduit. Wash fluid in the second conduit is moved by a pump means 43, into contact with the sensors.

Figure 34:
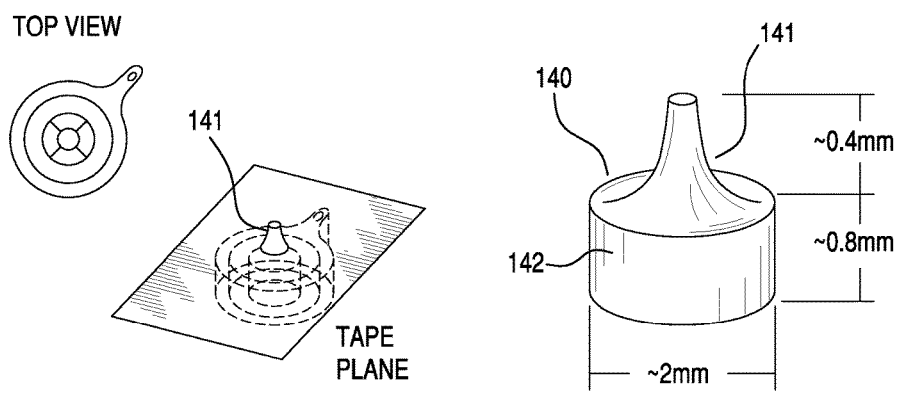
FIG. 34 illustrates an exemplary segment forming means.

The air segment (meniscus) or segments are produced within a conduit by any suitable means, including a passive means, an embodiment of which is shown in FIG. 34 and described in detail in U.S. Pat. No. 7,682,833 (referenced above), or an active means including a transient lowering of the pressure within a conduit using pump means whereby air is drawn into the conduit through a flap or valve. The air segment is extremely effective at clearing the sample-contaminated fluid from conduit 15. The efficiency of the rinsing of the sensor region is greatly enhanced by the introduction of one or more air segments. The leading and/or trailing edges of air segments are passed one or more times over the sensors to rinse and resuspend extraneous material that may have been deposited from the sample. Extraneous material includes any material other than specifically bound analyte or analyte/antibody-enzyme conjugate complex. However, in accordance with various embodiments of the invention, the washing or rinsing step is not sufficiently protracted or vigorous so as to promote substantial resuspension of the magnetically susceptible beads or dissociation of specifically bound analyte or analyte/antibody-enzyme conjugate complex from the beads. For measurement, a further portion of fluid containing the enzyme substrate is placed over the beads on the immunosensors, and the current or potential, as appropriate to the mode of operation, is recorded as a function of time.

FIG. 34 illustrates the construction of a specific means for passively introducing an air segment into the sample fluid. Within the base of the immunosensor is recess 140 comprising a tapered portion 141 and a cylindrical portion 142 that are connected. The tapered portion is in fluid connection with a hole of similar diameter with the tape gasket (FIG. 32) that separates the base (FIG. 33) and cover (FIGS. 30 and 31) of the assembled immunosensor cartridge. The recess contains an absorbent material that, upon contact with fluid, withdraws a small quantity of fluid from a conduit thereby passively introducing an air segment into the conduit. The volume of the recess and the amount and type of material within it may be adjusted to control the size of the air segment introduced. Specific absorbent materials include, but are not limited to, glass filter and a laminate comprising a 3 μm Versapor® filter (i.e., acrylic copolymer membrane cast on a nonwoven nylon support) bonded by sucrose to a 60% viscose chiffon layer.

Example 3

Magnetic Immunosensing Device and Method of Use

The present example describes one of the methods of use of a cartridge. In this embodiment, the cartridge includes a closeable valve, located between the immunosensor and the waste chamber. For a cTnI assay, a blood sample is first introduced into the sample chamber of the cartridge. In the following time sequence, time zero (t=0) represents the time at which the cartridge is inserted into the cartridge reading device. Times are given in minutes. Between t=0 and t=1.5, the cartridge reading device makes electrical contact with the sensors through electrical contact pads and performs certain diagnostic tests. Insertion of the cartridge perforates the foil pouch introducing fluid into the second conduit, as previously described herein. The diagnostic tests determine whether fluid or sample is present in the conduits using the conductivity electrodes, determine whether electrical short circuits are present in the electrodes, and ensure that the sensor and ground (e.g., reference/counter) electrodes are thermally equilibrated to, preferably, 37° C. prior to the analyte determination.

Between t=1.5 and t=6.75, a metered portion of the sample, preferably between about 4 μL and about 200 μL, more preferably between about 4 μL and about 20 μL, and most preferably about 7 μL, is used to contact the sensor. The edges defining the forward and trailing edges of the sample are reciprocally moved over the conductivity sensor region at a frequency that is preferably between 0.2 to 5.0 Hz, and is most preferably 0.7 Hz. During this time, the enzyme-antibody conjugate and magnetically susceptible beads dissolve within the sample. The amount of enzyme-antibody conjugate that is coated onto the conduit is selected to yield a concentration when dissolved that is preferably higher than the highest anticipated cTnI concentration, and is most preferably six times higher than the highest anticipated cTnI concentration in the sample.

Between t=6.75 and t=10.0, the sample is moved to the immunosensor for capture of the magnetically susceptible beads. As shown in FIGS. 30-33, the sample is moved into the waste chamber via closeable valve 41, wetting the closeable valve and causing it to close. The seal created by the closing of the valve 41 permits the first pump means to be used to control motion of fluid from conduit 11 to conduit 15. After the valve 41 closes and the remaining sample is locked in the post analysis conduit, the analyzer plunger retracts from the flexible diaphragm of the pump mean, creating a partial vacuum in the sensor conduit. This forces the analysis fluid through the small hole in the tape gasket 31 and into a short transecting conduit in the base, 13 and 14. The analysis fluid is then pulled further and the front edge of the analysis fluid is oscillated across the surface of the immunosensor chip in order to shear the sample near the walls of the conduit. The conductivity sensor on the chip is used to control this process.

The efficiency of the wash is optimally further enhanced by introduction into the fluid of one or more meniscus or air segment. As previously described, the air segment may be introduced by either active or passive means. Fluid is then forcibly moved towards sensor chip by the partial vacuum generated by reducing the mechanical pressure exerted upon paddle 6, causing the "T" region of the sensor channel in the vicinity of the transecting conduit to fill with analysis fluid. The T region of the sensor channel optionally has a higher channel height resulting in a meniscus with a smaller radius of curvature. Further away from the T region towards the post-analytical conduit, the conduit height is optionally smaller. The analysis fluid passively flows from the T region towards this low conduit height region, thereby washing the conduit walls. This passive leak allows further effective washing of the T region using a minimal volume of fluid and without displacing the magnetically susceptible beads. In this embodiment, the fluid located within the second conduit also contains a substrate for the enzyme. In other embodiments, amendment of the fluid using dried substrate within the second conduit may be utilized.

Following the positioning of a final segment of fluid over the sensor, measurement of the sensor response is recorded and the concentration of analyte is determined. Specifically, at least one sensor reading of a sample is made by rapidly placing over the sensor a fresh portion of fluid containing a substrate for the enzyme. Rapid displacement both rinses away product previously formed, and provides a new substrate to the electrode. Repetitive signals are averaged to produce a measurement of higher precision, and also to obtain a better statistical average of the baseline, represented by the current immediately following replacement of the solution over the immunosensor.

Example 4

Magnetic Immunosensing Device

Figure 35:
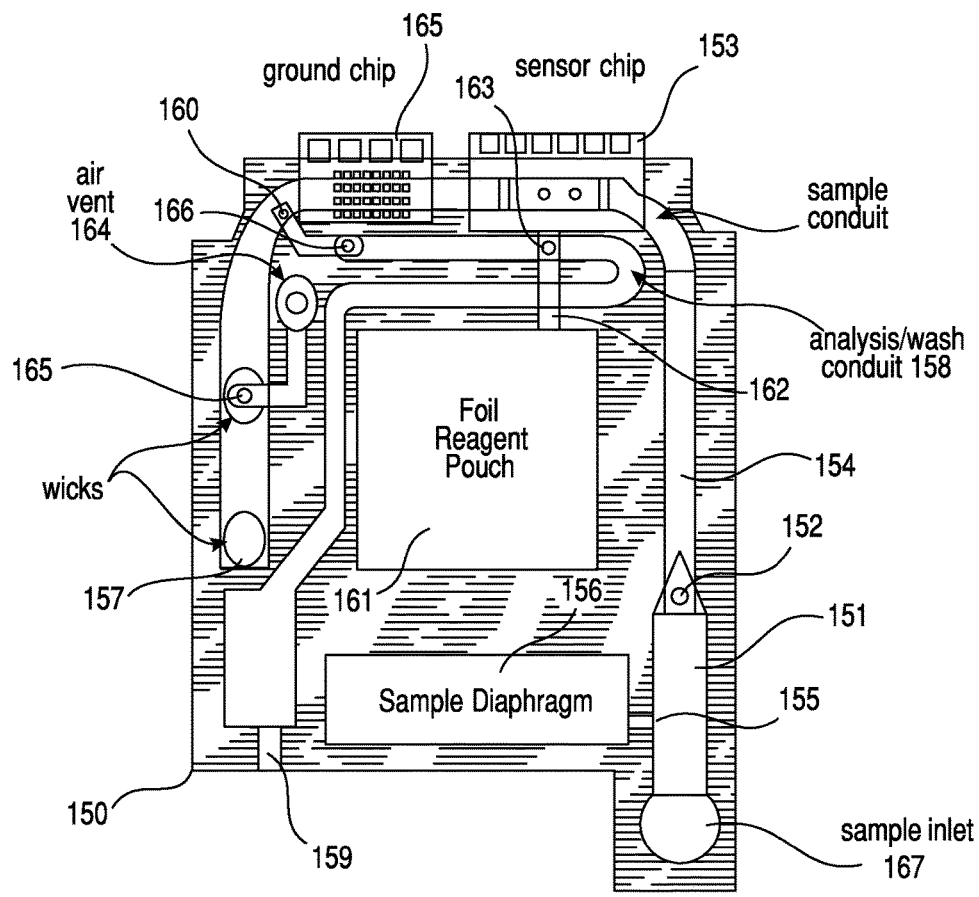
FIG. 35 is a top view of one embodiment of an immunosensor cartridge.

Referring now to FIG. 35, there is shown a top view of a magnetic immunosensor cartridge in accordance with one embodiment of the present invention. Cartridge 150 comprises a base and a top portion, preferably constructed of plastic. The two portions are connected by a thin, adhesive gasket or thin pliable film. As in previous embodiments, the assembled cartridge comprises a sample chamber 151 into which a sample containing an analyte of interest is introduced via sample inlet 152. A metered portion of the sample is delivered to the sensor chip 153 (comprising an integrated magnetic layer) via the sample conduit 154 (first conduit) by the combined action of a capillary stop 152, preferably formed by a 0.012" laser cut hole in the gasket or film that connects the two portions of the cartridge, and an entry point 155 located at a predetermined point within the sample chamber whereby air is introduced by the action of a pump means, such as a paddle pushing upon a sample diaphragm 156. After magnetic capture of the beads on the immunosensor, the sample is moved to vent 157, which contains a wicking material that absorbs the sample and thereby seals the vent closed to the further passage of liquid or air. The wicking material is preferably a cotton fiber material, a cellulose material, or other hydrophilic material having pores. It is important in the present application that the material is sufficiently absorbent (i.e., possesses sufficient wicking speed) that the valve closes within a time period that is commensurate with the subsequent withdrawal of the sample diaphragm actuating means, so that the sample is not subsequently drawn back into the region of the immunosensor.

In specific embodiments of the invention, there is provided a wash conduit (second conduit) 158, connected at one end to a vent 159 and at the other end to the sample conduit at a point 160 of the sample conduit that is located between vent 157 and immunosensor chip 153. Upon insertion of the cartridge into a reading apparatus, a fluid is introduced into conduit 158. Preferably, the fluid is present initially within a foil pouch 161 that is punctured by a pin when an actuating means applies pressure upon the pouch. There is also provided a short conduit 162 that connects the fluid to conduit 154 via a small opening in the gasket 163. A second capillary stop initially prevents the fluid from reaching capillary stop 160, so that the fluid is retained within conduit 158.

After vent 157 has closed, the pump means is actuated, creating a lowered pressure within conduit 154. Air vent 164, preferably comprising a small flap cut in the gasket or a membrane that vibrates to provide an intermittent air stream, provides a means for air to enter conduit 158 via a second vent 165. The second vent 165 preferably also contains wicking material capable of closing the vent if wetted, which permits subsequent depression of sample diaphragm 156 to close vent 165, if required. Simultaneously with the actuation of sample diaphragm 156, fluid is drawn from conduit 158, through capillary stop 160, into conduit 154. Because the flow of fluid is interrupted by air entering vent 164, at least one air segment (e.g., a segment or stream of segments) is introduced.

Further withdrawal of sample diaphragm 156 draws the liquid containing at least one air segment back across the sensing surface of sensor chip 153. The presence of air-liquid boundaries within the liquid enhances the rinsing of the sensor chip surface to remove remaining sample. Preferably, the movement of the sample diaphragm 156 is controlled in conjunction with signals received from the conductivity electrodes housed within the sensor chip adjacent to the analyte sensors. In this way, the presence of liquid over the sensor is detected, and multiple readings can be performed by movement of the fluid in discrete steps.

It is advantageous in this embodiment to perform analyte measurements when only a thin film of fluid coats the magnetically susceptible beads on the immunosensors, ground chip 165, and a contiguous portion of the wall of conduit 154 between the sensors and ground electrode. A suitable film is obtained by withdrawing fluid by operation of the sample diaphragm 156, until the conductimetric sensor located next to the sensor indicates that bulk fluid is no longer present in that region of conduit 154. It has been found that measurement can be performed at very low (nA) currents, and the potential drop that results from increased resistance of a thin film between ground chip and sensor chip (compared to bulk fluid) is not significant.

The ground chip 165 is preferably a silver/silver chloride reference electrode and acts effectively as both a counter and reference electrode in an amperometric measurement. It is advantageous, in this embodiment of the invention, to avoid air segments, which easily form upon the relatively hydrophobic silver chloride surface, to pattern the ground chip as small regions of silver/silver chloride interspersed with more hydrophilic regions, such as a surface of silicon dioxide. Thus, a preferred ground electrode (counter and reference electrode combined) configuration comprises an array of silver/silver chloride squares densely arranged and interspersed with silicon dioxide. There is a further advantage in the avoidance of unintentional segments if the regions of silver/silver chloride are somewhat recessed.

Figure 36:
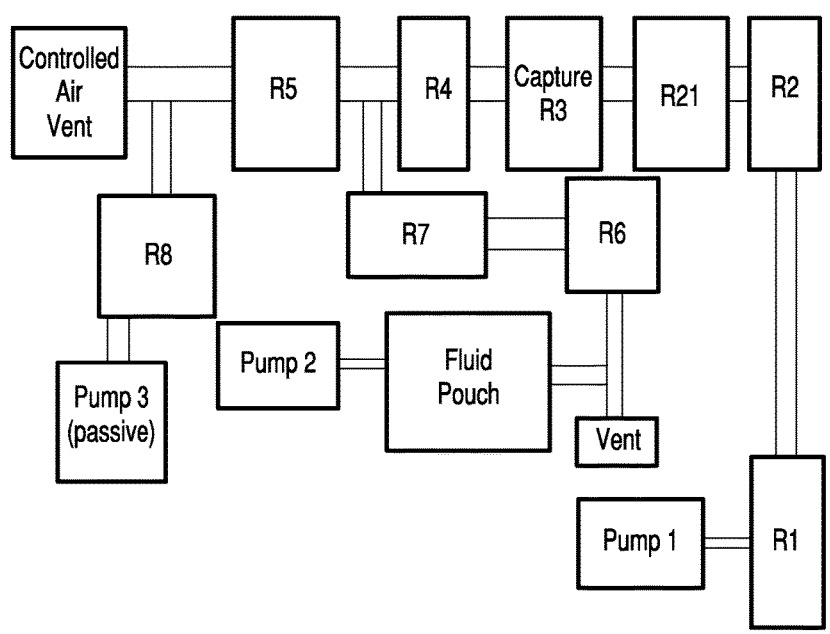
FIG. 36 is a schematic view of the fluidics of one embodiment of an immunosensor cartridge.

Referring now to FIGS. 7 and 36, there is shown a schematic view of the fluidics of the preferred embodiment of an immunosensor cartridge. Regions R1-R7 represent specific regions of the conduits associated with specific operational functions. In particular, R1 represents the sample chamber; R2 the sample conduit whereby a metered portion of the sample is transferred to the capture region, and in which the sample is optionally amended with a substance coated upon the walls of the conduit (e.g., magnetically susceptible beads with antibody to the analyte and antibody conjugate); R21 represents a region for mixing and sample oscillation; R3 represents the magnetic capture region, which houses the immunosensors; R4 and R5 represent portions of the first conduit that are optionally used for further amendment of fluids with substances coated onto the conduit wall, whereby more complex assay schemes are achieved; R6 represents the portion of the second conduit into which fluid is introduced upon insertion of the cartridge into a reading apparatus; R7 comprises a portion of the conduit located between capillary stops 160 and 166 (shown in FIG. 35), in which further amendment can occur; and R8 represents the portion of conduit 154 located between point 160 and vent 157, which can further be used to amend liquids contained within.

Example 5

Magnetic Immunosensor System

This example addresses the coordination of fluidics and analyte measurements as a system. In the analysis sequence, a user places a sample into the cartridge, places the cartridge into the analyzer and in about 1 minute to about 20 minutes, a quantitative measurement of one or more analytes is performed. Referring to FIGS. 35 and 36, the following is a non-limiting example of a sequence of events that occur during the analysis:

1) A 25 to 50 μL sample is introduced in the sample inlet 167 and fills chamber 151 to capillary stop 152 formed by a 0.012" laser cut hole in the adhesive tape holding the cover and base components together. The user then seals the inlet and places the cartridge into the analyzer. Magnetically susceptible beads having antibodies to the analyte of interest and optionally a labeled conjugate antibody to the analyte may be provided in a dry coating on the walls of chamber 151 such that they dissolve into the sample once the sample is introduced therein. In an alternative embodiment, either or both the magnetically susceptible beads and the labeled conjugate antibody may be provided in a dry coating within conduit 154.

2) The analyzer makes contact with the cartridge, and a motor driven plunger presses onto the foil pouch 161, forcing the wash/analysis fluid out into a central conduit 158.

3) A separate motor driven plunger contacts the sample diaphragm 156, pushing a measured segment of the sample along the sample conduit (from reagent region R1 to R2 and R21). The sample position is detected via one or more conductivity sensors. The immunosensor chip is located in capture region R3.

4) The sample is oscillated by means of the sample diaphragm 156 in the R21 region in a predetermined and controlled fashion for a controlled time to promote binding of analyte to the magnetically susceptible beads and to the antibody conjugate.

5) The sample is pushed towards the waste region of the cartridge (R8) and comes in contact with a passive pump 157 in the form of a cellulose or similar absorbent wick. The action of wetting this wick seals the wick to air flow, thus eliminating its ability to vent excess pressure generated by the sample diaphragm 156. The active vent thereby becomes the "controlled air vent" of FIG. 36.

6) Rapid evacuation of the sample conduit (effected by withdrawing the motor driven plunger from the sample diaphragm 156) forces a mixture of air (from the vent) and wash/analysis fluid from the second conduit to move into the inlet located between R5 and R4. By repeating the rapid evacuation of the sample conduit, a series of air separated fluid segments are generated, which are pulled across the sensor chip towards the sample inlet (from R4 to R3 to R21 to R2 and R1). This process washes the sensor free of excess reagents and wets the sensor with reagents appropriate for the analysis. In certain embodiments, the wash/analysis fluid that originates in the foil pouch can be further amended by addition of reagents in R7 and R6 within the central wash/analysis fluid conduit.

7) The wash/analysis fluid segment is drawn at a slower speed towards the sample inlet to yield an immunosensor chip with the retained magnetically susceptible beads, which contains only a thin layer of the analysis fluid. The electrochemical analysis is performed at this point. The preferred method of analysis is amperometry, but potentiometry or impedance detection is also used.

8) The mechanism retracts, allowing the cartridge to be removed from the analyzer.

While the present invention has been described in terms of various preferred embodiments, those skilled in the art will recognize that modifications, substitutions, omissions and changes can be made to such embodiments without departing from the spirit and scope of the present invention.

What is claimed is:

1. A magnetic immunosensing device for detecting an analyte in a sample, comprising:
 a sample entry port for receiving the sample,
 a sample entry chamber in fluid communication with the sample entry port;
 a dry reagent comprising magnetically susceptible beads coated with an antibody to the analyte in the sample, wherein the dry reagent is present in the device as a coating in the sample entry port or the sample entry chamber, and is dissolved into the sample upon receiving the sample in the sample entry port or the sample entry chamber;
 a first conduit comprising a first portion in fluid communication with the sample entry chamber;
 a substantially planar chip positioned in a second portion of the conduit in fluid communication with the first portion of the first conduit, the chip comprising:
  a sensing electrode positioned in the second portion of the first conduit to detect activity of an electroactive species caused by binding of the analyte to the antibody and generate a sensor response; and
  a conductivity sensor positioned in the second portion of the first conduit and adjacent to the sensing electrode to monitor a position of the sample within the second portion of the first conduit relative to the sensing electrode;
 a sample diaphragm in communication with the sample entry chamber via a second conduit, wherein the sample diaphragm is capable of forcing air through the second conduit causing the sample and the beads to move from the sample entry chamber into the second portion of the first conduit and over the chip;
 an analyzer comprising a motor driven plunger to move the sample through the conduit, wherein the analyzer is in contact with the sample diaphragm; and
 a magnet that is either a permanent magnet or an electromagnet having a magnetic field of greater than 0.1 Tesla, wherein the magnet is positioned proximate to the chip for attracting the beads in the second portion of the first conduit substantially proximate to the sensing electrode and substantially retaining the beads at the sensing electrode surface during removal of unbound sample and washing of the sensing electrode with a wash fluid.

2. The device of claim 1, wherein the magnet is the permanent magnet.

3. The device of claim 1, wherein the magnet is the electromagnet.

4. The device of claim 1, wherein the sensing electrode is microfabricated.

5. The device of claim 1, wherein the sample is selected from the group consisting of blood, plasma, serum, urine, interstitial fluid and cerebrospinal fluid.

6. The device of claim 1, wherein the sample is amended with an anticoagulant.

7. The device of claim 1, wherein the permanent magnet or the electromagnet is positioned in a non-coplanar position relative to said chip.

8. The device of claim 1, wherein the permanent magnet is selected from the group consisting of samarium cobalt (SmCo) alloy, aluminum nickel cobalt alloy (AlNiCo) and ferrite.

9. The device of claim 1, wherein the permanent magnet comprises neodymium iron boron (NdFeB) alloy.

10. The device of claim 1, wherein the permanent magnet comprises $Nd_2Fe_{14}B$.

11. The device of claim 1, wherein the permanent magnet or the electromagnet is a bulk magnet.

12. The device of claim 1, wherein the permanent magnet or the electromagnet is a substantially cylindrical bulk magnet.

13. The device of claim 1, wherein the permanent magnet or the electromagnet is a substantially cylindrical bulk magnet, having a diameter in the range of about 0.1 mm to about 5 mm and a length of about 0.1 mm to about 5 mm.

14. The device of claim 1, wherein the permanent magnet or the electromagnet is positioned to yield a bead event horizon in the conduit in the range of up to about 200 μm from the region of the sensing electrode.

15. The device of claim 1, wherein the beads comprise ferrite.

16. The device of claim 1, wherein the beads comprise magnetite ($Fe_3O_4$).

17. The device of claim 1, wherein the beads comprise a magnetically susceptible core with a polymer coating.

18. The device of claim 1, wherein the beads have an average particle size of from 0.01 μm to 20 μm.

19. The device of claim 1, wherein the beads have an average particle size of from 0.1 μm to 5 μm.

20. The device of claim 1, wherein the beads have an average particle size of from 0.2 μm to 1.5 μm.

21. The device of claim 1, wherein the sensing electrode is amperometric.

22. The device of claim 1, wherein the sensing electrode is a gold microarray.

23. The device of claim 1, wherein the conduit has a height of about 0.2 mm to about 5 mm and a width of about 0.2 mm to about 5 mm.

24. The device of claim 1, wherein the conduit has a uniform cross-sectional area.

25. The device of claim 1, wherein the conduit has a non-uniform cross-sectional area.

26. The device of claim 1, wherein the analyte is selected from the group consisting of cardiac troponin I, troponin T, a troponin complex, human chorionic gonadotropin, BNP, creatine kinase, creatine kinase subunit M, creatine kinase subunit B, creatine kinase MB (CK-MB), proBNP, NT-proBNP, myoglobin, myosin light chain, galectin-3, and modified fragments thereof.

27. The device of claim 1, wherein the analyte is selected from the group consisting of beta-HCG, TSH, ultra hTSH II, TT3, TT4, FT3, FT4, myeloperoxidase, D-dimer, CRP, NGAL, PSA, LH, FSH, prolactin, progesterone, estradiol, DHEA-S, AFP, CA 125 II, CA 125, CA 15-3, CA 19-9, CA 19-9XR, CEA, thyroxine (T4), triiodothyronine (T3), T-up-take, Tg, anti-Tg, anti-TPO, ferritin, cortisol, insulin, HBsAg, HCV Ag/Ab combo, HCV core Ag, anti-HCV, AUSAB (anti-HBs), CORE, CORE-M, SHBG, iPTH, theophylline, sirolimus, tacrolimus, anti-HAV, anti-HAV IgM, HAVAB, HAVAB-M, HAVAB-M2.0, HAVAB-G, HAVAB 2.0, HAVAB 2.0 Quant, IgM, CMV IgM, CMV IgG, â-2-microglobulin, digitoxin, HBe, anti-HBe, HBeAg, HIV 1/2gO, HIV Ag/Ab combo, testosterone, SCC, vitamin B12, folate, syphilis, anti-HBc, rubella IgG, rubella IgM, homocysteine, MPO, cytomegalovirus (CMV) IgG Avidity, toxo IgG avidity, toxo IgG, toxo IgM, C-peptide, vitamin D, HTLV I/II, total âhCG, progesterone, estradrogen, prolactin, myoglobin, tPSA, fPSA, carbamazepine (CBZ), digoxin, gentamicin, NAPA, phenytoin, phenobarbital, valproic acid, vancomycin, procaine, quinidine, tobramycin, methamphetamine (METH), amphetamine (AMPH), barbituates, benzodiazepine, cannabis, cocaine, methadone, opiates, PCP, acetaminophen, ethanol, salicylates, tricyclics, holoTc, anti-CCP, HbA1c, barbs-U and modified fragments thereof.

28. A kit for performing an analyte immunoassay in a whole blood sample, comprising:
    a magnetic immunosensing device comprising:
    a sample entry port for receiving the sample,
    a sample entry chamber in fluid communication with the sample entry port;
    a dry reagent comprising magnetically susceptible beads coated with an antibody to the analyte in the sample, wherein the dry reagent is present in the device as a coating in the sample entry port or the sample entry chamber, and is dissolved into the sample upon receiving the sample in the sample entry port or the sample entry chamber;
    a first conduit comprising a first portion in fluid communication with the sample entry chamber;
    a substantially planar chip positioned in a second portion of the conduit in fluid communication with the first portion of the first conduct, the chip comprising:
    a sensing electrode positioned in the second portion of the conduit to detect activity of an electroactive species caused by binding of the analyte to the antibody and generate a sensor response;
    a conductivity sensor positioned in the second portion of the first conduit and adjacent to the sensing electrode to monitor a position of the sample within the second portion of the first conduit relative to the sensing electrode;
    a sample diaphragm in communication with the sample entry chamber via a second conduit, wherein the sample diaphragm is capable of forcing air through the second conduit causing the sample and the beads to move from the sample entry chamber into the second portion of the first conduit and over the chip;
    an analyzer comprising a motor driven plunger to move the sample through the conduit, wherein the analyzer is in contact with the sample diaphragm;
    a magnet that is either a permanent magnet or an electromagnet having a magnetic field of greater than 0.1 Tesla, wherein the magnet is positioned proximate to the chip for attracting the beads substantially proximate to the sensing electrode and substantially retaining the beads at the sensing electrode surface; and
    a reader for receiving the immunosensor cartridge and comprising:
    a motor driven plunger to apply pressure to the sample diaphragm and force the air through the second conduit causing the sample and the beads to move from the sample entry chamber into the second portion of the first conduit and over the chip; and an electrical contact to receive the sensor response from the sensing electrode, wherein the reader is capable of determining a concentration of the analyte from the sensor response.

29. The kit of claim 28, wherein the magnet is the permanent magnet.

30. The kit of claim 28, wherein the magnet is the electromagnet.

31. The kit of claim 28, wherein the immunoassay is a sandwich assay.

32. The kit of claim 28, wherein the immunoassay is a competitive assay.

33. The kit of claim 28, wherein over 50 wt. % of the beads are retained at the sensing electrode surface.

34. The kit of claim 28, wherein over 75 wt. % of the beads are retained at the sensing electrode surface.

* * * * *